(12) United States Patent
Yamaguchi et al.

(10) Patent No.: US 8,394,540 B2
(45) Date of Patent: Mar. 12, 2013

(54) ANODE AND METHOD OF MANUFACTURING SAME, SECONDARY BATTERY AND METHOD OF MANUFACTURING SAME, AND SULFONE COMPOUND

(75) Inventors: Hiroyuki Yamaguchi, Fukushima (JP); Masayuki Ihara, Fukushima (JP); Tadahiko Kubota, Kanagawa (JP)

(73) Assignee: Sony Corporation, Tokyo (JP)

( * ) Notice: Subject to any disclaimer, the term of this patent is extended or adjusted under 35 U.S.C. 154(b) by 649 days.

(21) Appl. No.: 12/336,071

(22) Filed: Dec. 16, 2008

(65) Prior Publication Data

US 2009/0263726 A1 Oct. 22, 2009

(30) Foreign Application Priority Data

Dec. 28, 2007 (JP) ................. 2007-339154

(51) Int. Cl.
*H01M 6/16* (2006.01)
(52) U.S. Cl. ........ 429/324; 429/220; 429/221; 429/326; 429/327; 429/328
(58) Field of Classification Search .................. 429/220, 429/221, 326, 327, 328, 324
See application file for complete search history.

(56) References Cited

U.S. PATENT DOCUMENTS

| 6,432,583 B1 * | 8/2002 | Fukuda et al. ............. 429/231.4 |
| 6,534,220 B2 * | 3/2003 | Garbe ........................... 429/342 |
| 2002/0197537 A1 * | 12/2002 | Kim et al. ..................... 429/340 |
| 2005/0142448 A1 * | 6/2005 | Kim et al. ..................... 429/326 |
| 2009/0092892 A1 * | 4/2009 | Yamaguchi et al. .......... 429/125 |

FOREIGN PATENT DOCUMENTS

| JP | 2000-268830 | 9/2000 |
| JP | 2002-008718 | 1/2002 |
| JP | 2002-056891 | 2/2002 |
| JP | 2006-156331 | 6/2006 |
| JP | 2006-286312 | 10/2006 |
| JP | 2006-294373 | 10/2006 |
| JP | 2006-294519 | 10/2006 |
| JP | 2007-042387 | 2/2007 |
| WO | WO 2007/136046 A1 * | 11/2007 |

* cited by examiner

*Primary Examiner* — Patrick Ryan
*Assistant Examiner* — Alex Usyatinsky
(74) *Attorney, Agent, or Firm* — SNR Denton US LLP

(57) ABSTRACT

A secondary battery capable of improving the cycle characteristics is provided. The secondary battery includes a cathode and an anode oppositely arranged with a separator in between, and an electrolytic solution. At least one of the cathode, the anode, the separator, and the electrolytic solution contains a sulfone compound having a carbonate group and a sulfonyl group.

8 Claims, 8 Drawing Sheets

ANODE AND METHOD OF MANUFACTURING SAME, SECONDARY BATTERY AND METHOD OF MANUFACTURING SAME, AND SULFONE COMPOUND

CROSS REFERENCES TO RELATED APPLICATIONS

The present invention contains subject matter related to Japanese Patent Application JP 2007-339154 filed in the Japanese Patent Office on Dec. 28, 2007, the entire contents of which being incorporated herein by reference.

BACKGROUND OF THE INVENTION

1. Field of the Invention

The present invention relates to an anode in which an anode active material layer is provided on an anode current collector and a method of manufacturing the anode, a secondary battery using the anode and a method of manufacturing the secondary battery, and a sulfone compound having a sulfonyl group.

2. Description of the Related Art

In the past, in various fields, a sulfone compound having a sulfonyl group has been widely used. As an example, in the field of electrochemical devices, to improve the electric performance and the like, various sulfone compounds are contained as an additive in the electrolytic solution or the like.

Of the electrochemical devices, in the field of secondary batteries used as a power source for portable electronic devices such as mobile phones and notebook personal computers, researches to improve battery characteristics such as capacity characteristics and cycle characteristics are actively made. Specially, a secondary battery using insertion and extraction of lithium for charge and discharge reaction (lithium ion secondary battery) and a secondary battery using precipitation and dissolution of lithium metal (so-called lithium metal secondary battery) are extremely prospective, since such a lithium ion secondary battery and such a lithium metal secondary battery are able to provide a higher energy density than the existing lead battery and the existing nickel cadmium battery.

In the lithium ion secondary battery using insertion and extraction of lithium, almost no lithium contributing to the charge and discharge reaction is precipitated on the electrode as metal lithium. Thus, the metal lithium is not likely dropped from the electrode and deactivated. Therefore, the lithium ion secondary battery is regarded as a battery that has more superior capacity reproducibility in the case where charge and discharge are repeated and provides more stable charge and discharge characteristics than the lithium metal secondary battery using precipitation and dissolution of lithium. The lithium ion secondary battery includes an electrolytic solution together with a cathode and an anode. The electrolytic solution contains a solvent and an electrolyte salt.

In the lithium ion secondary battery, as the sulfone compound used as an additive of the electrolytic solution, several sulfone compounds have been already known. Specifically, to improve low temperature discharge characteristics and ambient temperature storage characteristics, it has been proposed that an aromatic compound having ester sulfonate and ester carboxylate covalently such as o-methane methyl benzoate sulfonate is used (for example, refer to Japanese Unexamined Patent Application Publication No. 2000-268830). Further, to improve load characteristics in the case where the battery is stored at high temperature, it has been proposed that an anhydride of sulfonic acid and carboxylic acid such as a sulfobenzoic acid anhydride is used, or phenyl sulfonic acid such as sulfobenzoic acid or a phenyl sulfonic metal such as benzendisulfonic dipotassium or the like is used (for example, refer to Japanese Unexamined Patent Application Publication Nos. 2002-008718 and 2002-056891). Further, to improve high temperature cycle characteristics, it has been proposed that a sulfur-containing compound such as diphenyl sultone and 1,3-propane sultone is used (for example, refer to Japanese Unexamined Patent Application Publication No. 2006-294519). Further, to improve charge and discharge efficiency, it has been proposed that a monomer having a sulfonic ion group such as sodium vinylsulfonate is used (for example, refer to Japanese Unexamined Patent Application Publication No. 2007-042387). In this case, it has been also proposed that a polymer compound formed by polymerizing the monomer having the sulfonic ion group is provided as a coat on the surface of the electrode.

SUMMARY OF THE INVENTION

However, the existing sulfone compound is not sufficient yet to improve the electric performance of the electrochemical devices. In particular, for the secondary battery, since sufficient cycle characteristics have not been obtained yet, it leaves sufficient room for improving the cycle characteristics.

In view of the foregoing, in the invention, it is desirable to provide an anode capable of improving the cycle characteristics and a method of manufacturing the anode, a secondary battery and a method of manufacturing the secondary battery, and a sulfone compound.

According to an embodiment of the invention, there is provided an anode having a coat on an anode active material layer provided on an anode current collector, in which the coat contains a sulfone compound having a carbonate group and a sulfonyl group. According to an embodiment of the invention, there is provided a method of manufacturing an anode having a coat on an anode active material layer provided on an anode current collector, wherein the coat is formed on the anode active material layer by using a solution containing a sulfone compound having a carbonate group and a sulfonyl group.

According to an embodiment of the invention, there is provided a secondary battery including a cathode and an anode oppositely arranged with a separator in between and an electrolytic solution. At least one of the cathode, the anode, the separator, and the electrolytic solution contains a sulfone compound having a carbonate group and a sulfonyl group.

According to an embodiment of the invention, there is provided a method of manufacturing a secondary battery including a cathode and an anode arranged oppositely with a separator in between and an electrolytic solution, in which at least one of the cathode, the anode, the separator, and the electrolytic solution contains a sulfone compound having a carbonate group and a sulfonyl group.

According to an embodiment of the invention, there is provided a sulfone compound having a carbonate group and a sulfonyl group.

The sulfone compound of the embodiment of the invention has the carbonate group and the sulfonyl group. Thus, in the case where the sulfone compound is used as an additive of an electrolytic solution or a coat of an electrode or the like in an electrochemical device, the chemical stability of the electrolytic solution, the coat or the like is improved. Thereby, according to the anode using the sulfone compound of the embodiment of the invention or the method of manufacturing the anode, since the coat containing the sulfone compound is formed on the anode active material layer, the chemical stability of the anode is improved. Thus, in the case where the anode is used for an electrochemical device such as a battery, an electrode reactant is efficiently inserted in the anode and extracted from the anode, and the anode is less reacted with other material such as an electrolytic solution. Therefore, according to the anode of the embodiment of the invention, the secondary battery using the method of manufacturing the anode, and the method of manufacturing the secondary battery, since the foregoing sulfone compound is contained in at least one of the cathode, the anode, the separator, and the electrolytic solution, the cycle characteristics are able to be improved. In this case, the foregoing sulfone compound is contained in at least one of the cathode, the anode, and the separator. Therefore, in the case where dipping treatment or coating treatment is performed by using the solution containing the sulfone compound, the sulfone compound is able to be easily contained, compared to a case that a method necessitating special environmental conditions such as reduced pressure environment.

Other and further objects, features and advantages of the invention will appear more fully from the following description.

DETAILED DESCRIPTION OF THE PREFERRED EMBODIMENT

Figure 1:
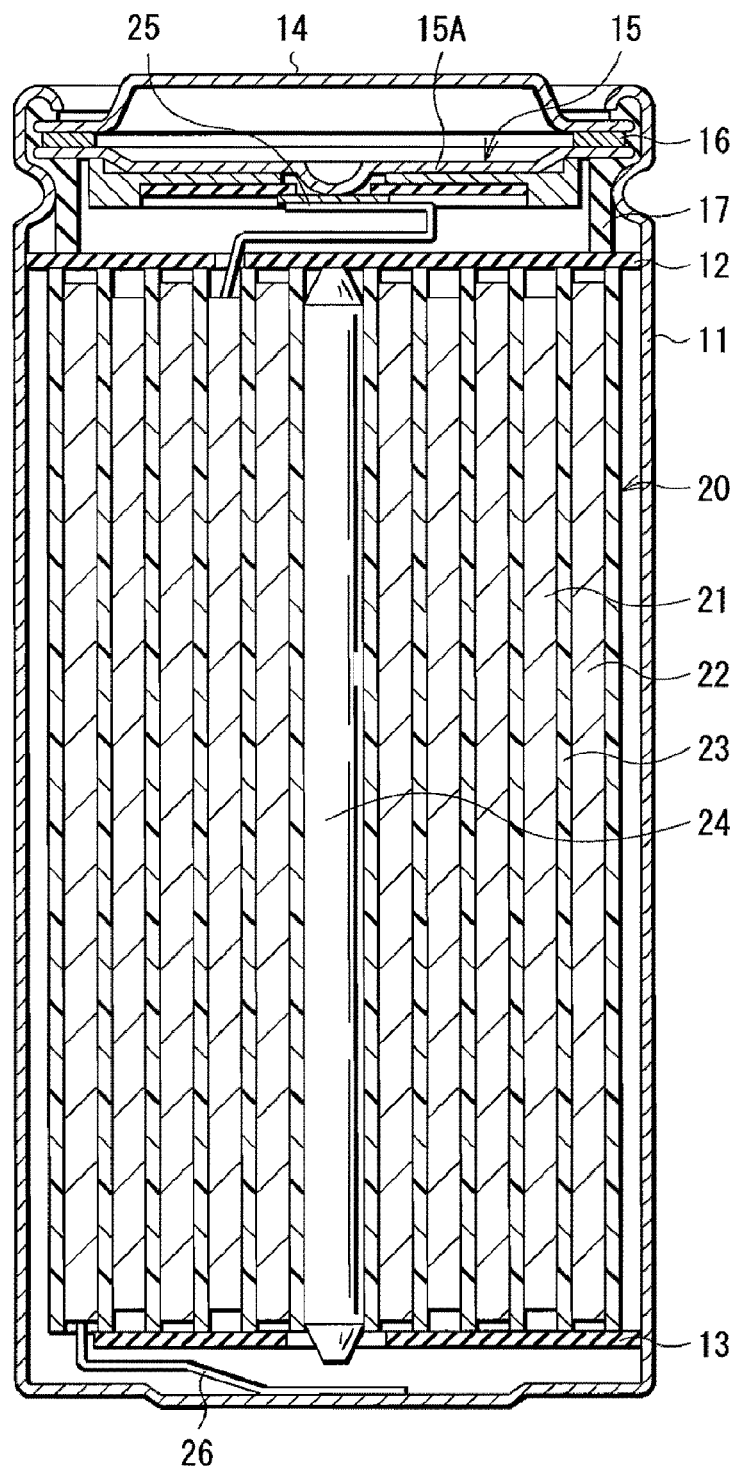
FIG. 1 is a cross sectional view showing a structure of a first secondary battery using a sulfone compound according to an embodiment of the invention.

An embodiment of the invention will be hereinafter described in detail with reference to the drawings.

A sulfone compound according to an embodiment of the invention is used for, for example, an electrochemical device such as a secondary battery. The sulfone compound has a carbonate group (—O—CO—O—) and a sulfonyl group (—SO$_2$—). In the case where the sulfone compound is used for the electrochemical device, for example, the sulfone compound may be dispersed as an additive in a liquid such as an electrolytic solution, or may be formed as a coat on the surface of a solid such as an electrode.

Since the sulfone compound has the carbonate group and the sulfonyl group, chemical stability of the foregoing electrolytic solution, the foregoing coat and the like is improved, which contributes to improving electric performance of the electrochemical device.

The sulfone compound may have any structure as a whole, as long as the sulfone compound has the carbonate group and the sulfonyl group. In this case, the number of carbonate groups may be one or more. The number of sulfonyl groups may be one or more. The carbonate group may be directly bonded to the sulfonyl group, or the carbonate group and the sulfonyl group may be indirectly bonded to each other via some group.

In particular, for example, the sulfone compound preferably has the structure shown in Chemical formula 1 or Chemical formula 2, since thereby the sulfone compound may be easily synthesized, and provides high effect. The structure shown in Chemical formula 2 corresponds to a structure in which R1 and R2 shown in Chemical formula 1 are single-bonded.

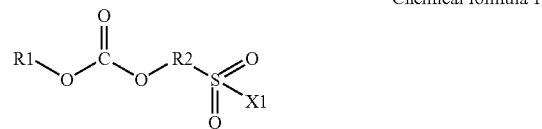

Chemical formula 1

In the formula, R1 is an alkyl group with the carbon number in the range from 1 to 8, both inclusive or an alkyl halide group with the carbon number in the range from 1 to 8, both inclusive. R2 is an alkylene group with the carbon number in the range from 1 to 8, both inclusive or an alkylene halide group with the carbon number in the range from 1 to 8, both inclusive. X1 is a halogen group, a hydroxyl group, or a group expressed by —OM1. M1 is an alkali metal, an alkali earth metal, or a silyl ester group.

Chemical formula 2

In the formula, R3 is an alkylene group with the carbon number in the range from 1 to 8, both inclusive or an alkylene halide group with the carbon number in the range from 1 to 8, both inclusive. R4 is a trivalent group obtained by detaching one hydrogen group from an alkylene group with the carbon number in the range from 1 to 8, both inclusive or a trivalent group obtained by detaching one hydrogen group or one halogen group from an alkylene halide group. X2 is a halogen group, a hydroxyl group, or a group expressed by —OM2. M2 is an alkali metal, an alkali earth metal, or a silyl ester group.

"Alkyl halide group" described for R1 in Chemical formula 1 is a group obtained by substituting at least one hydrogen in the alkyl group with halogen. Similarly, "alkylene halide group" described for R2 in Chemical formula 1 and R3 in Chemical formula 2 is a group obtained by substituting at least one hydrogen in the alkylene group with halogen.

Further, "trivalent group obtained by detaching one hydrogen group or one halogen group from an alkylene halide group" described for R4 in Chemical formula 2 is a group obtained by detaching one hydrogen group or one halogen group from a group obtained by substituting at least one hydrogen in an alkylene group with halogen (divalent group). The detached group may be a hydrogen group or a halogen group.

Further, "silyl ester group" descried for X1 in Chemical formula 1 is a group expressed by —Si(R)$_3$, and R is an alkyl group. In this case, three Rs may be identical to or different from each other. The same is applied to X2 in Chemical formula 2.

In particular, the reason why the carbon number of R1 and R2 in Chemical formula 1 is 8 or less is as follows. If the carbon number is more than 8, the solubility of the sulfone compound becomes high. Thus, in the case where the sulfone compound is used for an electrochemical device, the sulfone compound may be excessively dissolved in an organic solvent or the like. Further, the halogen group described for Chemical formula 1 is not particularly limited. Specially, a fluorine group (—F) is preferable. Thereby, higher effect is obtained than other type of halogen group such as a chlorine group (—Cl). The same is applied to the carbon numbers of R3 and R4 and the halogen group type in Chemical formula 2.

As a sulfone compound having the structure shown in Chemical formula 1, for example, the compounds shown in Chemical formula 3 to Chemical formula 6 are cited. X1 is a fluorine group in Chemical formula 3, a hydroxyl group (—OH) in Chemical formula 4, —OLi in which M1 is lithium in Chemical formula 5, and —O—Si(CH$_3$)$_3$ in which M1 is a trimethyl silyl group in Chemical formula 6.

Chemical formula 3

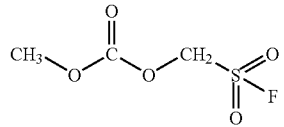
(1)

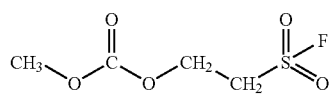
(2)

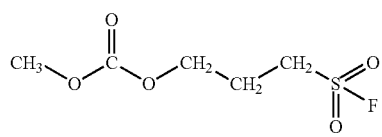
(3)

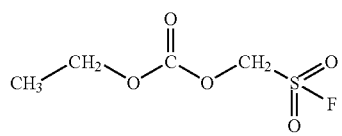
(4)

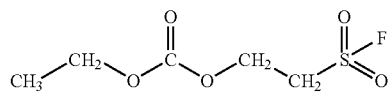
(5)

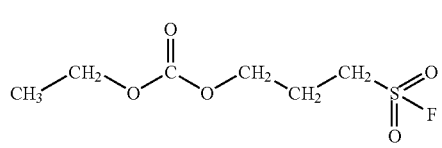
(6)

Chemical formula 4

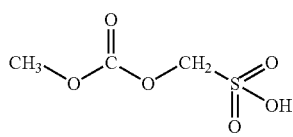
(1)

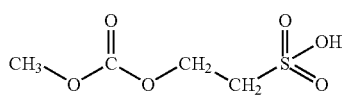
(2)

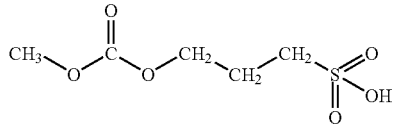
(3)

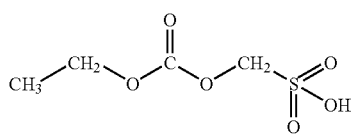
(4)

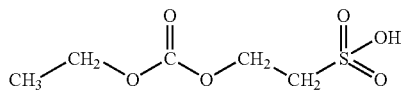
(5)

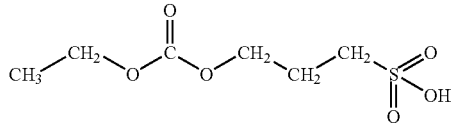
(6)

Chemical formula 5

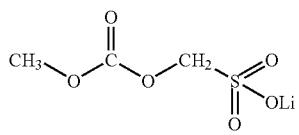
(1)

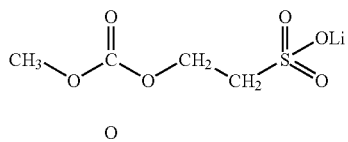
(2)

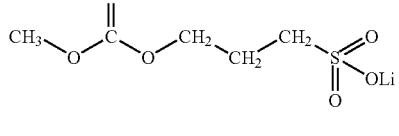
(3)

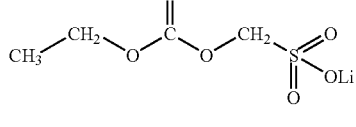
(4)

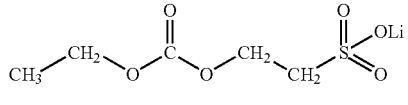
(5)

(6)
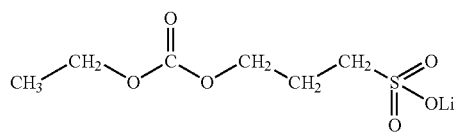

Chemical formula 6

(1)
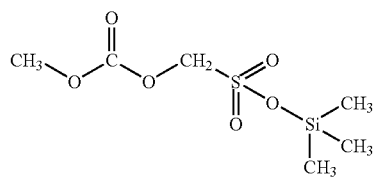

(2)
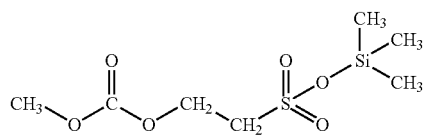

(3)
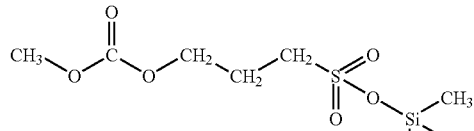

(4)
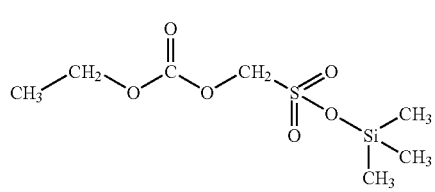

(5)
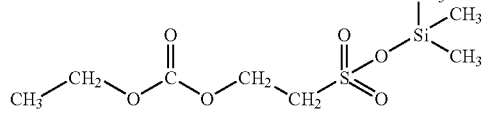

(6)
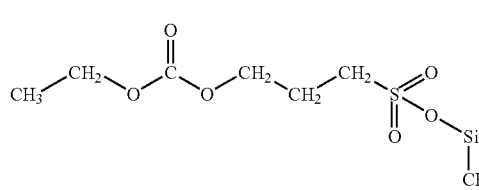

As a sulfone compound having the structure shown in Chemical formula 2, for example, the compounds shown in Chemical formulas 7 to 10 are cited. X2 is a fluorine group in Chemical formula 7, a hydroxyl group in Chemical formula 8, —OLi in which M2 is lithium in Chemical formula 9, and —O—Si(CH$_3$)$_3$ in which M2 is a trimethyl silyl group in Chemical formula 10.

Chemical formula 7

(1)
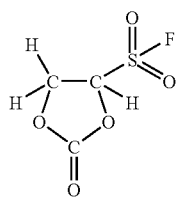

(2)
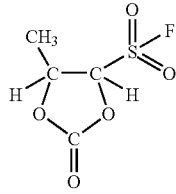

(3)
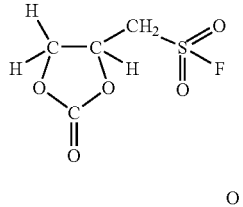

(4)
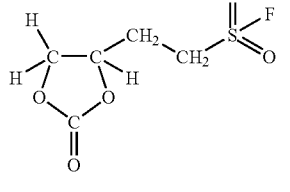

(5)
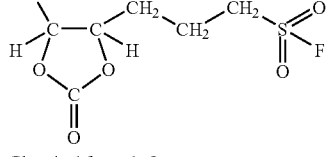

Chemical formula 8

(1)
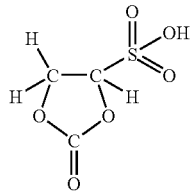

(2)
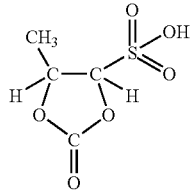

(3)
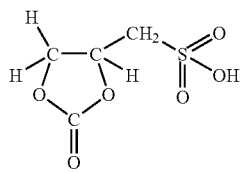

-continued

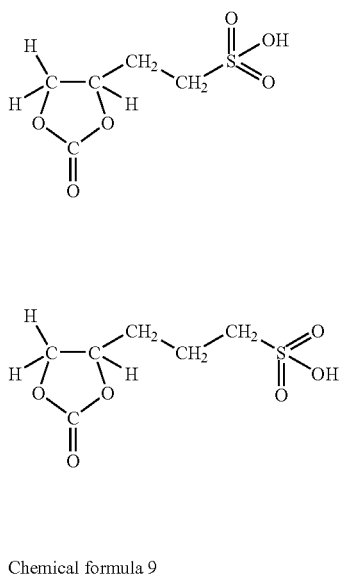

Chemical formula 9

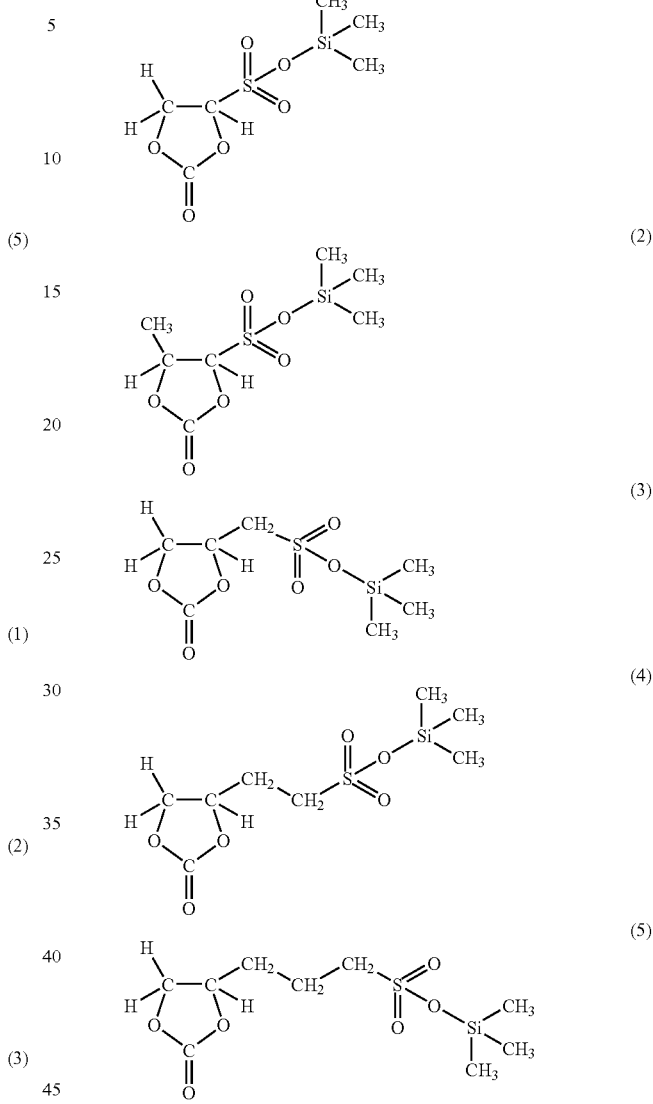

Chemical formula 10

It is needless to say that the sulfone compound is not limited to the case having the structure shown in Chemical formula 1 or Chemical formula 2, as long as the sulfone compound has the carbonate group and the sulfonyl group.

A description will be given for confirmation. In Chemical formulas 5 and 9, the case that M1 or M2 is monovalent alkali metal (lithium) is shown as an example. Thus, the sulfone compound has only one portion other than M1 or M2 (portion having the carbonate group and the sulfonyl group). Meanwhile, in the case where M1 or M2 is divalent or more, the sulfone compound has two or more portions other than M1 or M2. As an example, in the case where M1 or M2 is divalent alkali earth metal (magnesium (Mg), calcium (Ca) or the like), the sulfone compound has two portions other than M1 or M2.

The sulfone compound has the carbonate group and the sulfonyl group. Thus, in the case where the sulfone compound is used as an additive of the electrolytic solution or the like or a coat of the electrode or the like for an electrochemical device, the chemical stability of the electrolytic solution, the coat or the like is improved. Therefore, the sulfone compound is able to contribute to improve the electric performance of the electrochemical device. More specifically, in the case where the sulfone compound is used for a secondary battery as the electrochemical device, the sulfone compound is able to contribute to improve the cycle characteristics.

In particular, in the case where the sulfone compound has the structure shown in Chemical formula 1 or Chemical formula 2, the solubility is suppressed. Thus, if the sulfone compound is used together with an organic solvent or the like for an electrochemical device, the function to improve the chemical stability of the electrolytic solution, the coat and the like is able to be stably demonstrated.

Next, a description will be given of a usage example of the foregoing sulfone compound. Taking a secondary battery as an example of electrochemical devices, the sulfone compound is used for the secondary battery as follows.

The secondary battery described below includes a cathode and an anode opposed with a separator in between and an electrolytic solution. For example, the secondary battery is a lithium ion secondary battery in which the anode capacity is expressed based on insertion and extraction of lithium as an electrode reactant. The cathode has a cathode active material layer on a cathode current collector. The anode has an anode active material layer on an anode current collector. The electrolytic solution contains a solvent and an electrolyte salt dissolved in the solvent.

In the secondary battery, at least one component among the cathode, the anode, the separator, and the electrolytic solution contains the foregoing sulfone compound. Thereby, since the chemical stability of the component containing the sulfone compound is improved, decomposition reaction of the electrolytic solution is prevented.

In the case where the cathode and the anode contain the sulfone compound, a coat containing the sulfone compound is provided on the cathode active material layer or the anode active material layer. In the case where the electrolytic solution contains the sulfone compound, the sulfone compound is dispersed in the solvent. In this case, the entire sulfone compound may be dissolved, or only part thereof may be dissolved. In the case where the separator contains the sulfone compound, a coat containing the sulfone compound is provided on a single face or the both faces of the separator.

The number of components containing the sulfone compound may be one among the cathode, the anode, the separator, and the electrolytic solution. However, two or more components preferably contain the sulfone compound, and all the components more preferably contain the sulfone compound. Thereby, decomposition reaction of the electrolytic solution is further prevented. Specially, if one component containing the sulfone compound is selected, the cathode or the separator is preferable to the electrolytic solution, and the anode is more preferable. Further, if two components containing the sulfone compound are selected, the combination of the anode and the separator is preferable. Thereby, in any case, higher effect is able to be obtained.

The secondary battery type (battery structure) is not particularly limited. A description will be hereinafter given of a detailed structure of the secondary battery in the case that the anode contains the sulfone compound taking a cylindrical secondary battery and a laminated film secondary battery as a battery structure.

First Secondary Battery

Figure 2:
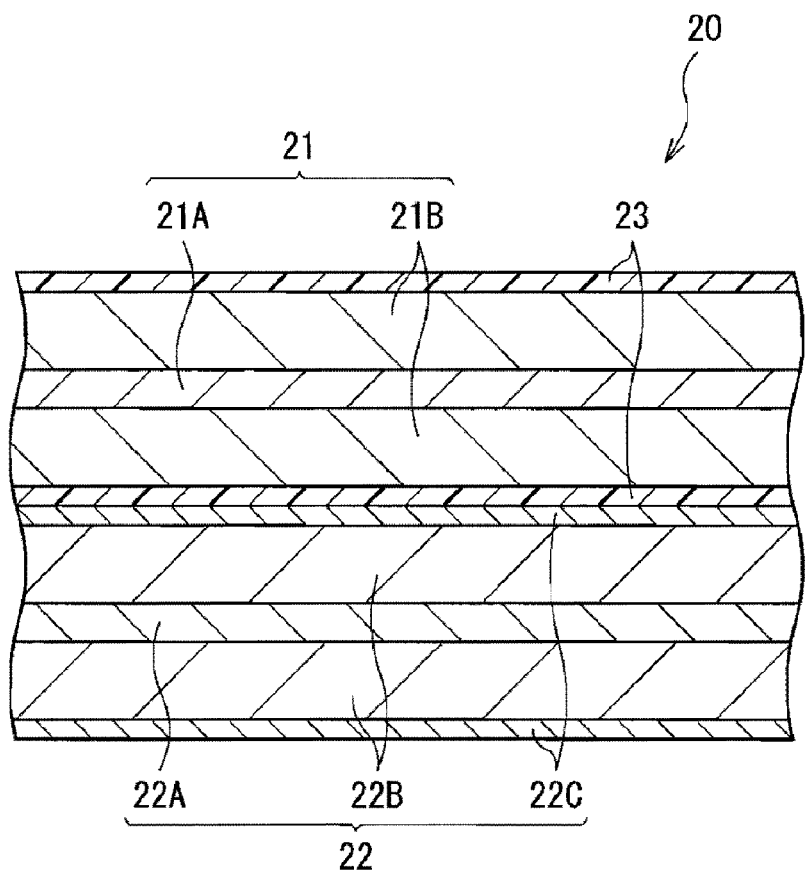
FIG. 2 is a cross sectional view showing an enlarged part of the spirally wound electrode body shown in FIG. 1.

FIG. 1 and FIG. 2 show a cross sectional structure of a first secondary battery. FIG. 2 shows an enlarged part of a spirally wound electrode body 20 shown in FIG. 1.

The secondary battery mainly contains the spirally wound electrode body 20 in which a cathode 21 and an anode 22 are spirally wound with a separator 23 in between, and a pair of insulating plates 12 and 13 inside a battery can 11 in the shape of an approximately hollow cylinder. The battery structure using the cylindrical battery can 11 is a so-called cylindrical type.

The battery can 11 has, for example, a hollow structure in which one end thereof is closed and the other end thereof is opened, and is made of a metal material such as iron, aluminum, and an alloy thereof. In the case where the battery can 11 is made of iron, for example, plating by nickel or the like may be provided. The pair of insulating plates 12 and 13 is arranged to sandwich the spirally wound electrode body 20 in between from above and below and to extend perpendicularly to the spirally wound periphery face.

At the open end of the battery can 11, a battery cover 14, and a safety valve mechanism 15 and a PTC (Positive Temperature Coefficient) device 16 provided inside the battery cover 14 are attached by being caulked with a gasket 17. Inside of the battery can 11 is thereby hermetically sealed. The battery cover 14 is made of, for example, a metal material similar to that of the battery can 11. The safety valve mechanism 15 is electrically connected to the battery cover 14 with the PTC device 16 in between. In the safety valve mechanism 15, in the case where the internal pressure of the battery becomes a certain level or more by internal short circuit, external heating or the like, a disk plate 15A flips to cut the electric connection between the battery cover 14 and the spirally wound electrode body 20. As a temperature rises, the PTC device 16 increases the resistance and thereby limits a current to prevent abnormal heat generation resulting from a large current. The gasket 17 is made of, for example, an insulating material and its surface is coated with asphalt.

A center pin 24 may be inserted in the center of the spirally wound electrode body 20. In the spirally wound electrode body 20, a cathode lead 25 made of a metal material such as aluminum is connected to the cathode 21, and an anode lead 26 made of a metal material such as nickel is connected to the anode 22. The cathode lead 25 is electrically connected to the battery cover 14 by being welded to the safety valve mechanism 15. The anode lead 26 is electrically connected to the battery can 11 by being welded to the battery can 11.

The cathode 21 has a structure in which, for example, a cathode active material layer 21B is provided on the both faces of a cathode current collector 21A having a pair of faces. However, the cathode active material layer 21B may be provided on only a single face of a cathode current collector 21A.

The cathode current collector 21A is made of, for example, a metal material such as aluminum, nickel, and stainless.

The cathode active material layer 21B contains, as a cathode active material, one or more cathode materials capable of inserting and extracting lithium. If necessary, the cathode active material layer 21B may contain other material such as a binder and an electrical conductor.

As the cathode material capable of inserting and extracting lithium, for example, a lithium-containing compound is preferable, since thereby a high energy density is obtained. As the lithium-containing compound, for example, a complex oxide containing lithium and a transition metal element or a phosphate compound containing lithium and a transition metal element are cited. Specially, a compound containing at least one selected from the group consisting of cobalt, nickel, manganese, and iron as a transition metal element is preferable, since thereby a higher voltage is able to be obtained. The chemical formula thereof is expressed as, for example, $Li_xM1O_2$ or $Li_yM2PO_4$. In the formula, M1 and M2 represent one or more transition metal elements. Values of x and y vary according to the charge and discharge state, and are generally in the range of $0.05 \leqq x \leqq 1.10$ and $0.05 \leqq y \leqq 1.10$.

As the complex oxide containing lithium and a transition metal element, for example, a lithium cobalt complex oxide ($Li_xCoO_2$), a lithium nickel complex oxide ($Li_xNiO_2$), a lithium nickel cobalt complex oxide ($Li_xNi_{1-z}CO_zO_2$ ($z<1$)), a lithium nickel cobalt manganese complex oxide ($Li_xNi_{(1-v-w)}CO_vMn_wO_2$) ($v+w<1$)), lithium manganese complex oxide having a spinel structure ($LiMn_2O_4$) and the like are cited. Specially, a complex oxide containing cobalt is preferable, since thereby a high capacity is obtained and superior cycle characteristics are obtained. Further, as the phosphate compound containing lithium and a transition metal element, for example, lithium iron phosphate compound ($LiFePO_4$), a lithium iron manganese phosphate compound ($LiFe_{1-u}Mn_uPO_4$ ($u<1$)) and the like are cited.

In addition, as the cathode material capable of inserting and extracting lithium, for example, an oxide such as titanium oxide, vanadium oxide, and manganese dioxide; a disulfide such as titanium disulfide and molybdenum sulfide; a chalcogenide such as niobium selenide; sulfur; a conductive polymer such as polyaniline and polythiophene are cited.

It is needless to say that the cathode material capable of inserting and extracting lithium may be a material other than the foregoing compounds. Further, the two or more of the foregoing series of cathode materials may be used by arbitral mixture.

As the electrical conductor, for example, a carbon material such as graphite, carbon black, acetylene black, and Ketjen black is cited. Such a carbon material may be used singly, or a plurality thereof may be used by mixture. The electrical conductor may be a metal material, a conductive polymer molecule or the like as long as the material has the electric conductivity.

As the binder, for example, a synthetic rubber such as styrene-butadiene rubber, fluorinated rubber, and ethylene propylene diene; or a polymer material such as polyvinylidene fluoride are cited. One thereof may be used singly, or a plurality thereof may be used by mixture.

The anode 22 has a structure in which, for example, an anode active material layer 22B and a coat 22C are provided on the both faces of an anode current collector 22A having a pair of opposed faces. However, the anode active material layer 22B may be provided on only a single face of the anode current collector 22A. The same is applied to the coat 22C.

The anode current collector 22A is made of, for example, a metal material such as copper, nickel, and stainless. The surface of the anode current collector 22A is preferably roughened. Thereby, due to so-called anchor effect, contact characteristics between the anode current collector 22A and the anode active material layer 22B are improved. In this case, it is enough that at least a region of the surface of the anode current collector 22A that is opposed to the anode active material layer 22B is roughened. As a roughening method, for example, a method of forming fine particles by electrolytic treatment and the like are cited. The electrolytic treatment is a method for providing unevenness by forming the fine particles on the surface of the anode current collector 22A by electrolytic method in an electrolytic bath. A copper foil provided with the electrolytic treatment is generally called "electrolytic copper foil."

The anode active material layer 22B contains, as an anode active material, one or more anode materials capable of inserting and extracting lithium. If necessary, the anode active material layer 22B may contain other material such as a binder and an electrical conductor. Details of the binder and the electrical conductor, for example, are similar to those described for the cathode 21.

As the anode material capable of inserting and extracting lithium, for example, a material that is capable of inserting and extracting lithium, and has at least one of metal elements and metalloid elements as an element is cited, since a high energy density is thereby obtained. Such an anode material may be a simple substance, an alloy, or a compound of a metal element or a metalloid element, or may have one or more phases thereof at least in part. In the invention, "alloys" include an alloy containing one or more metal elements and one or more metalloid elements, in addition to an alloy composed of two or more metal elements. Further, "alloy" may contain a nonmetallic element. The texture thereof includes a solid solution, a eutectic crystal (eutectic mixture), an intermetallic compound, and a texture in which two or more thereof coexist.

As the foregoing metal element or the foregoing metalloid element, for example, a metal element or a metalloid element capable of forming an alloy with lithium is cited. Specifically, magnesium, boron (B), aluminum, gallium (Ga), indium (In), silicon, germanium (Ge), tin, lead (Pb), bismuth (Bi), cadmium (Cd), silver (Ag), zinc, hafnium (Hf), zirconium (Zr), yttrium (Y), palladium (Pd), platinum (Pt) and the like are cited. Specially, at least one of silicon and tin is preferable. Silicon and tin have the high ability to insert and extract lithium, and provide a high energy density.

As an anode material having at least one of silicon and tin, for example, the simple substance, an alloy, or a compound of silicon; the simple substance, an alloy, or a compound of tin; or a material having one or more phases thereof at least in part are cited.

As the alloy of silicon, for example, an alloy containing at least one selected from the group consisting of tin, nickel, copper, iron, cobalt, manganese, zinc, indium, silver, titanium, germanium, bismuth, antimony (Sb), and chromium as the second element other than silicon is cited. As the compound of silicon, for example, a compound containing oxygen or carbon (C) is cited, and may contain the foregoing second element in addition to silicon. Examples of the alloy or the compound of silicon include $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_5Si$, $FeSi_2$, $MnSi_2$, $NbSi_2$, $TaSi_2$, $VSi_2$, $WSi_2$, $ZnSi_2$, $SiC$, $Si_3N_4$, $Si_2N_2O$, $SiO_v$ ($0<v\leqq2$), $SnO_w$, ($0<w\leqq2$), LiSiO and the like.

As the alloy of tin, for example, an alloy containing at least one selected from the group consisting of silicon, nickel, copper, iron, cobalt, manganese, zinc, indium, silver, titanium, germanium, bismuth, antimony, and chromium as the second element other than tin is cited. As a compound of tin, for example, a compound containing oxygen or carbon is cited, and may contain the foregoing second element in addition to tin. Examples of the alloy or the compound of tin include $SnSiO_3$, LiSnO, $Mg_2Sn$ and the like.

In particular, as the anode material containing at least one of silicon and tin, for example, an anode material containing a second element and a third element in addition to tin as a first element is preferable. The second element is at least one selected from the group consisting of cobalt, iron, magnesium, titanium, vanadium (V), chromium, manganese, nickel, copper, zinc, gallium, zirconium, niobium (Nb), molybdenum, silver, indium, cerium (Ce), hafnium, tantalum (Ta), tungsten (W), bismuth, and silicon. The third element is at least one selected from the group consisting of boron, carbon, aluminum, and phosphorus (P). In the case where the second element and the third element are contained, the cycle characteristics are improved.

Specially, a SnCoC-containing material that contains tin, cobalt, and carbon as an element, in which the carbon content is in the range from 9.9 wt % to 29.7 wt %, both inclusive, and the cobalt ratio to the total of tin and cobalt (Co/(Sn+Co)) is in the range from 30 wt % to 70 wt %, both inclusive is preferable. In such a composition range, a high energy density is able to be obtained.

The SnCoC-containing material may further has other element according to needs. As other element, for example, silicon, iron, nickel, chromium, indium, niobium, germanium, titanium, molybdenum, aluminum, phosphorus, gallium, bismuth or the like is preferable. Two or more thereof may be contained, since thereby higher effect is obtained.

The SnCoC-containing material has a phase containing tin, cobalt, and carbon. Such a phase is preferably a low crystalline phase or an amorphous phase. The phase is a reaction phase capable of being reacted with lithium, and superior cycle characteristics are thereby obtained. The half-width of the diffraction peak obtained by X-ray diffraction of the phase is preferably 1.0 deg or more based on diffraction angle of $2\theta$ in the case where CuK$\alpha$ ray is used as a specific X ray, and the insertion rate is 1 deg/min. Thereby, lithium is more smoothly inserted and extracted, and reactivity with the electrolyte is decreased.

It is easily determined whether or not the diffraction peak obtained by X-ray diffraction of the phase corresponds to the reaction phase capable of being reacted with lithium by comparing an X-ray diffraction chart before the electrochemical reaction with lithium to an X-ray diffraction chart after the electrochemical reaction with lithium. For example, if the diffraction peak position in the X-ray diffraction chart after the electrochemical reaction with lithium is changed from the diffraction peak position in the X-ray diffraction chart before the electrochemical reaction with lithium, the diffraction peak obtained by X-ray diffraction of the phase corresponds to the reaction phase capable of being reacted with lithium. In this case, for example, the diffraction peak of the low crystalline or amorphous reaction phase is shown in the range from $2\theta=20$ deg to 50 deg. The low crystalline or amorphous reaction phase contains, for example, the foregoing respective elements. It is considered that the low crystalline or amorphous reaction phase is mainly realized by carbon.

The SnCoC-containing material may have a phase containing a simple substance of each element or part thereof, in addition to the low crystalline or the amorphous phase.

In particular, in the SnCoC-containing material, at least part of carbon as an element is preferably bonded to a metal element or a metalloid element as other element. Cohesion or crystallization of tin or the like is thereby prevented.

As a measurement method for examining bonding state of elements, for example, X-ray Photoelectron Spectroscopy (XPS) is cited. XPS is a method for examining element composition and element bonding state in the region up to several nm from the sample surface by irradiating the sample surface with soft X ray (in a commercial device, Al—K$\alpha$ ray or Mg—K$\alpha$ ray is used) and measuring motion energy of a photoelectron jumping out from the sample surface.

The bound energy of an inner orbit electron of an element is changed correlatively to the charge density on the element in an initial approximate manner. For example, in the case where the charge density of carbon element is decreased by interaction with an element existing in the vicinity thereof, an outer orbit electron such as 2p electron is decreased, and thus 1s electron of carbon element is subject to strong binding force by the orbit. That is, in the case where the charge density of the element is decreased, the bound energy becomes high.

In XPS, in the case where the bound energy becomes high, the peak is shifted to a higher energy region.

In XPS, in the case of graphite, the peak of 1s orbit of carbon (C1s) is shown in 284.5 eV in the apparatus in which energy calibration is made so that the peak of 4f orbit of gold atom (Au4f) is obtained in 84.0 eV. In the case of surface contamination carbon, the peak is observed at 284.8 eV. Meanwhile, in the case of higher charge density of carbon element, for example, in the case where carbon is bonded to an element that is more positive than carbon, the peak of C1s is observed in the region lower than 284.5 eV. That is, in the case where at least part of carbon contained in the SnCoC-containing material is bonded to the metal element, the metalloid element or the like as other element, the peak of the composite wave of C1s obtained for the SnCoC-containing material is observed in the region lower than 284.5 eV.

In performing XPS measurement, in the case where the surface is covered with surface contamination carbon, the surface is preferably slightly sputtered by an argon ion gun attached to an XPS device. Further, if the SnCoC-containing material as a measuring target exists in the anode 22, it is preferable that after the secondary battery is disassembled and the anode 22 is taken out, the anode 22 is preferably washed with a volatile solvent such as dimethyl carbonate in order to remove a low volatile solvent and an electrolyte salt existing on the surface of the anode 22. Such sampling is desirably performed under the inactive atmosphere.

Further, in XPS measurement, for example, the peak of C1s used for correcting the energy axis of spectrums. Since surface contamination carbon generally exists on a material surface, the peak of C1s of the surface contamination carbon is set to in 284.8 eV, which is used as an energy reference. In XPS measurement, the waveform of the peak of C1s obtained as a form including the peak of the surface contamination carbon and the peak of carbon in the SnCoC-containing material. Therefore, for example, by performing analysis by using commercially available software, the peak of the surface contamination carbon and the peak of carbon in the SnCoC-containing material are separated. In the analysis of the waveform, the position of the main peak existing on the lowest bound energy side is set to the energy reference (284.8 eV).

The SnCoC-containing material is able to be formed by, for example, mixing raw materials of respective elements, dissolving the resultant mixture in an electric furnace, a high frequency induction furnace, an arc melting furnace or the like and then solidifying the resultant. Otherwise, the SnCoC-containing material may be formed by various atomization methods such as gas atomizing and water atomizing; various roll methods; or a method using mechanochemical reaction such as mechanical alloying method and mechanical milling method. Specially, the method using mechanochemical reaction is preferable, since thereby the SnCoC-containing material becomes the low crystalline structure or the amorphous structure. In the method using the mechanochemical reaction, for example, a manufacturing apparatus such as a planetary ball mill apparatus and an attliter is able to be used.

As the raw material, a mixture of simple substances of the respective elements may be used, but an alloy is preferably used for part of elements other then carbon. In the case where carbon is added to the alloy and thereby the material is synthesized by the method using mechanical alloying method, the low crystalline structure or the amorphous structure is obtained and reaction time is reduced as well. The state of the raw material may be powder or a mass.

In addition to the SnCoC-containing material, an SnCoFeC-containing material having tin, cobalt, iron, and carbon as an element is also preferable. The composition of the SnCoFeC-containing material is able to be arbitrarily set. For example, as a composition in which the iron content is set small, it is preferable that the carbon content is in the range from 9.9 wt % to 29.7 wt %, both inclusive, the iron content is in the range from 0.3 wt % to 5.9 wt %, both inclusive, and the cobalt ratio to the total of tin and cobalt (Co/(Sn+Co)) is in the range from 30 wt % to 70 wt %, both inclusive. Further, for example, as a composition in which the iron content is set large, it is preferable that the carbon content is in the range from 11.9 wt % to 29.7 wt %, both inclusive, the total of cobalt and iron to the total of tin, cobalt, and iron ((Co+Fe)/(Sn+Co+Fe)) is in the range from 26.4 wt % to 48.5 wt %, both inclusive, and the cobalt ratio to the total of cobalt and iron (Co/(Co+Fe)) is in the range from 9.9 wt % to 79.5 wt %, both inclusive. In such a composition range, a high energy density is obtained. The crystallinity, the measurement method for examining bonding state of elements, the forming method of the SnCoFeC-containing material and the like are similar to those of the foregoing SnCoC-containing material.

The anode active material layer 22B using the simple substance, an alloy, or a compound of silicon; the simple substance, an alloy, or a compound of tin; or a material having one or more phases thereof at least in part as the anode material capable of inserting and extracting lithium is, for example, formed by using vapor-phase deposition method, liquid-phase deposition method, spraying method, coating method, firing method, or a combination of two or more of these methods. In this case, the anode current collector 22A and the anode active material layer 22B are preferably alloyed in at least part of the interface thereof. More specifically, at the interface thereof, the element of the anode current collector 22A may be diffused in the anode active material layer 22B; or the element of the anode active material layer 22B may be diffused in the anode current collector 22A; or these elements may be diffused in each other. Thereby, destruction due to expansion and shrinkage of the anode active material layer 22B in charge and discharge is prevented, and the electron conductivity between the anode current collector 22A and the anode active material layer 22B is improved.

As vapor-phase deposition method, for example, physical deposition method or chemical deposition method are cited. Specifically, vacuum evaporation method, sputtering method, ion plating method, laser ablation method, thermal Chemical Vapor Deposition (CVD) method, plasma CVD method and the like are cited. As liquid-phase deposition method, a known technique such as electrolytic plating and electroless plating is used. Coating method is a method in which, for example, after a particulate anode active material is mixed with a binder and the like, the resultant mixture is dispersed in a solvent and then coating is provided. Firing method is, for example, a method in which after coating is provided by coating method, heat treatment is provided at a temperature higher than the melting point of the binder or the like. For firing method, a known technique such as atmosphere firing method, reactive firing method, and hot press firing method is cited as well.

In addition to the foregoing, as the anode material capable of inserting and extracting lithium, for example, a carbon material is cited. As the carbon material, for example, graphitizable carbon, non-graphitizable carbon in which the spacing of (002) plane is 0.37 nm or more, or graphite in which the spacing of (002) plane is 0.34 nm or less and the like are cited. More specifically, pyrolytic carbon, coke, glassy carbon fiber, an organic polymer compound fired body, activated carbon, carbon black and the like are cited. Of the foregoing, the coke includes pitch coke, needle coke, petroleum coke and the like. The organic polymer compound fired body is obtained by firing and carbonizing a phenol resin, a furan resin or the like at an appropriate temperature. In the carbon material, the crystal structure change associated with inserting and extracting lithium is very small. Therefore, a high energy density is thereby obtained and superior cycle characteristics are thereby obtained. In addition, the carbon material also functions as an electrical conductor, and thus the carbon material is preferably used. The shape of the carbon material may be any of a fibrous shape, a spherical shape, a granular shape, and a scale-like shape.

As the anode material capable of inserting and extracting lithium, for example, a metal oxide, a polymer compound and the like capable of inserting and extracting lithium are cited. As the metal oxide, for example, iron oxide, ruthenium oxide, molybdenum oxide and the like are cited. As the polymer compound, for example, polyacetylene, polyaniline, polypyrrole and the like are cited.

It is needless to say that the anode material capable of inserting and extracting lithium may be a material other than the foregoing materials. Further, the two or more of the foregoing anode materials may be used by arbitrary mixture.

The anode active materiel made of the foregoing anode materials is composed of a plurality of particles. That is, the anode active material layer 22B has a plurality of anode active material particles. The anode active material particles are formed by, for example, the foregoing vapor-phase deposition method or the like. However, the anode active material particles may be formed by a method other than vapor-phase deposition method.

In the case where the anode active material particles are formed by deposition method such as vapor-phase deposition method, the anode active material particles may have a single layer structure formed by a single deposition step or may have a multilayer structure formed by a plurality of deposition steps. However, if the anode active material particles are formed by evaporation method associated with high heat in deposition, the anode active material particles preferably have a multilayer structure. In the case where the deposition step of the anode material is divided into several steps (a plurality of thin layers of the anode material are sequentially formed and deposited), time that the anode current collector 22A is exposed at high heat is reduced compared to a case that the deposition is performed in a single deposition step, accordingly the anode current collector 22A is less likely to be a subject to thermal damage.

The anode active material particles are grown, for example, in the thickness direction of the anode active material layer 22B from the surface of the anode current collector 22A. The anode active material particles are linked to the anode current collector 22A at the root thereof. In this case, it is preferable that the anode active material particles are formed by vapor-phase deposition method, and as described above, at least part of the interface with the anode current collector 22A is alloyed. More specifically, at the interface in between, the element of the anode current collector 22A may be diffused in the anode active material particles; or the element of the anode active material particles may be diffused in the anode current collector 22A; or these elements may be diffused in each other.

In particular, if necessary, the anode active material layer 22B preferably has an oxide-containing film covering the surface of the anode active material particles (region contacted with the electrolytic solution). Thereby, the oxide-containing film functions as a protection film to the electrolytic solution, and decomposition reaction of the electrolytic solution is prevented even if charge and discharge are repeated, resulting in improvement of the cycle characteristics. The oxide-containing film may cover part of the surface of the anode active material particles, or may cover the entire surface of the anode active material particles.

The oxide-containing film contains, for example, at least one oxide selected from the group consisting of silicon, germanium, and tin. Specially, the oxide-containing film preferably contains an oxide of silicon. Thereby, the oxide-containing film easily covers over the entire surface of the anode active material particles, and is able to provide superior protective action. It is needless to say that the oxide-containing film contains an oxide other than the foregoing oxide. The oxide-containing film is formed by, for example, vapor-phase deposition method or liquid-phase deposition method. Specially, liquid-phase deposition method such as liquid-phase precipitation method, solgel method, coating method, and dip coating method is preferable, and the liquid-phase precipitation method is more preferable, since thereby the surface of the anode active material particles is easily covered over a wide range.

If necessary, the anode active material layer 22B preferably has a metal material not being alloyed with the electrode reactant in a gap between the anode active material particles or in a gap in the particles. Thereby, the plurality of anode active materials are bound to each other with the metal material in between. In addition, in the case where the metal material exists in the foregoing gap, expansion and shrinkage of the anode active material layer 22B are prevented. Accordingly, the cycle characteristics are improved.

The metal material has, for example, a metal element not being alloyed with lithium as an element. As the metal element, for example, at least one selected from the group consisting of iron, cobalt, nickel, zinc, and copper is cited. Specially, cobalt is preferable, since thereby the metal material easily intrudes into the foregoing gap, and superior binding action is obtained. It is needless to say that the metal material may contain a metal element other than the foregoing metal elements. However, "metal material" herein is a comprehensive term, including not only a simple substance but also an alloy and a metal compound. The metal material is formed by, for example, vapor-phase deposition method or liquid-phase deposition method. Specially, the liquid-phase deposition method such as electrolytic plating method and electroless plating method is preferable, and the electrolytic plating method is more preferable. Thereby, the metal material easily intrudes into the foregoing gap, and the formation time thereof is reduced.

The anode active material layer 22B may have one of the foregoing oxide-containing film or the metal material, or may have both thereof. However, to further improve the cycle characteristics, the anode active material layer 22B preferably contains both thereof.

A description will be given in detail of the anode 22 with reference to FIG. 3 to FIG. 6.

Figure 3:
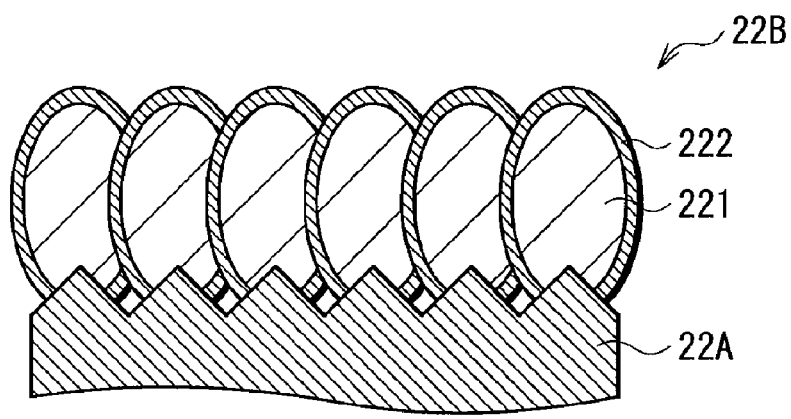
FIG. 3 is a cross sectional view showing an enlarged structure of the anode shown in FIG. 2.
Figure 4:
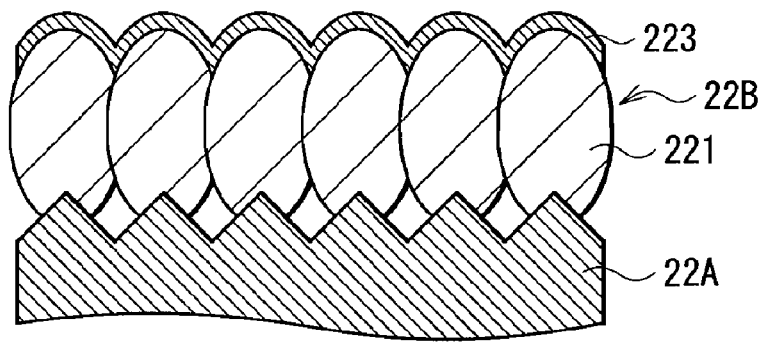
FIG. 4 is a cross sectional view showing a structure of an anode of a reference example.

First, a description will be given of a case that the anode active material layer 22B has the oxide-containing film together with the plurality of anode active material particles. FIG. 3 schematically shows a cross sectional structure of the anode 22 of the invention. FIG. 4 schematically shows a cross sectional structure of an anode of a reference example. FIG. 3 and FIG. 4 show a case that the anode active material particles have a single layer structure.

In the anode of the invention, as shown in FIG. 3, for example, when the anode material is deposited on the anode current collector 22A by vapor-phase deposition method such as evaporation method, a plurality of anode active material particles 221 are formed on the anode current collector 22A.

In this case, in the case where the surface of the anode current collector 22A is roughened and a plurality of projections (for example, fine particles formed by electrolytic treatment) exist on the surface thereof, the anode active material particles 221 are grown for every projection described above in the thickness direction. Thus, the plurality of anode active material particles 221 are arranged on the anode current collector 22A, and are linked to the surface of the anode current collector 22A at the root thereof. After that, for example, in the case where an oxide-containing film 222 is formed on the surface of the anode active material particle 221 by liquid-phase deposition method such as liquid-phase precipitation method, the oxide-containing film 222 covers almost entire surface of the anode active material particle 221, in particular, covers a wide range from the top to the root of the anode active material particle 221. Such a covering state in the wide range with the oxide-containing film 222 is a characteristic obtained in the case where the oxide-containing film 222 is formed by liquid-phase deposition method. That is, in the case where the oxide-containing film 222 is formed by liquid-phase deposition method, such covering action is applied not only to the top of the anode active material particle 221 but also to the root thereof. Accordingly, the anode active material particle 221 is covered with the oxide-containing film 222 down to the root thereof.

Meanwhile, in the anode of the reference example, as shown in FIG. 4, for example, in the case where the plurality of anode active material particles 221 are formed by vapor-phase deposition method and then an oxide-containing film 223 is formed by vapor-phase deposition method similarly, the oxide-containing film 223 covers only the top of the anode active material particle 221. Such a small range covered with the oxide-containing film 223 is a characteristic obtained in the case where the oxide-containing film 223 is formed by vapor-phase deposition method. That is, in the case where the oxide-containing film 223 is formed by vapor-phase deposition method, such covering action is applied to the top of the anode active material particle 221 but not applied to the root thereof. Accordingly, the anode active material particle 221 is not covered with the oxide-containing film 223 down to the root thereof.

In FIG. 3, the description has been given of a case that the anode active material layer 22B is formed by vapor-phase deposition method. However, in the case where the anode active material layer 22B is formed by sintering method or the like, an oxide-containing film is similarly formed to cover almost entire surface of the plurality of anode active material particles.

Figure 5A:
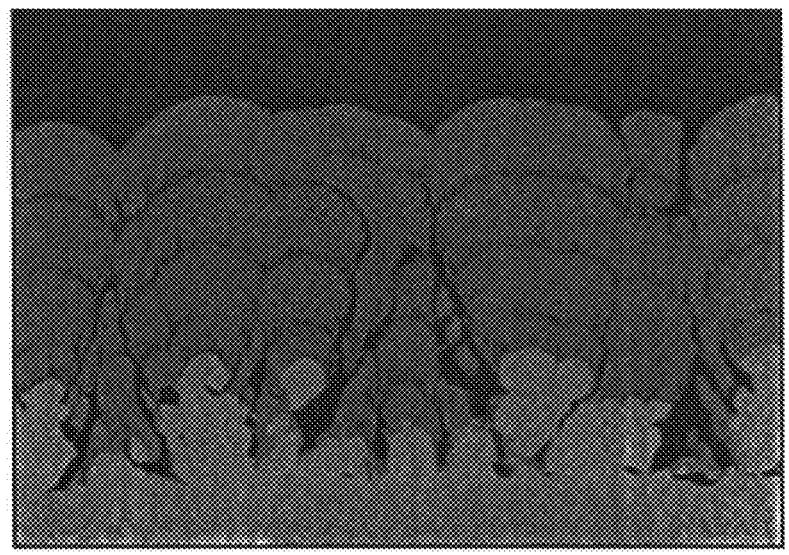
FIGS. 5A and 5B are an SEM photograph showing a cross sectional structure of the anode shown in FIG. 2 and a schematic view thereof.
Figure 5B:
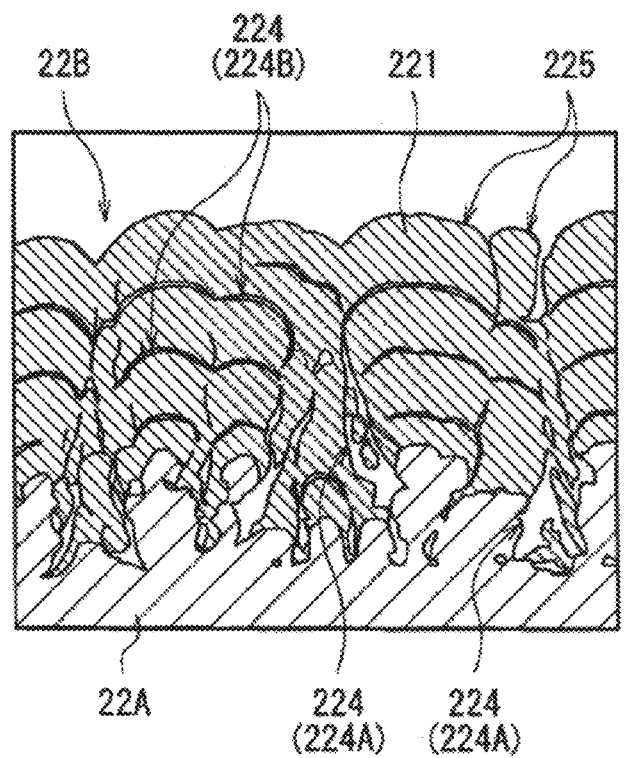

Next, a description will be given of a case that the anode active material layer 22B has the plurality of anode active material particles and the metal material not being alloyed with the electrode reactant. FIGS. 5A and 5B show an enlarged cross sectional structure of the anode 22. FIG. 5A is a Scanning Electron Microscope (SEM) photograph (secondary electron image), and FIG. 5B is a schematic drawing of the SEM image shown in FIG. 5A. FIGS. 5A and 5B show a case that the plurality of anode active material particles 221 have a multilayer structure in the particles.

In the case where the anode active material particles 221 have the multilayer structure, a plurality of gaps 224 are generated in the anode active material layer 22B due to the arrangement structure, the multilayer structure, and the surface structure of the plurality of anode active material particles 221. The gap 224 mainly includes two types of gaps 224A and 224B categorized according to the cause of generation. The gap 224A is a gap generated between adjacent anode active material particles 221. Meanwhile, the gap 224B is a gap generated between each layer in the anode active material particles 221.

On the exposed face (outermost surface) of the anode active material particle 221, a void 225 may be generated. As a fibrous minute projection (not shown) is generated on the surface of the anode active material particles 221, the void 225 is generated between the projections. The void 225 may be generated entirely over the exposed face of the anode active material particles 221, or may be generated in only part thereof. Since the foregoing fibrous minute projection is generated on the surface of the anode active material particles 221 every time the anode active material particles 221 are formed, the void 225 may be generated between each layer in addition to on the exposed face of the anode active material particles 221.

Figure 6A:
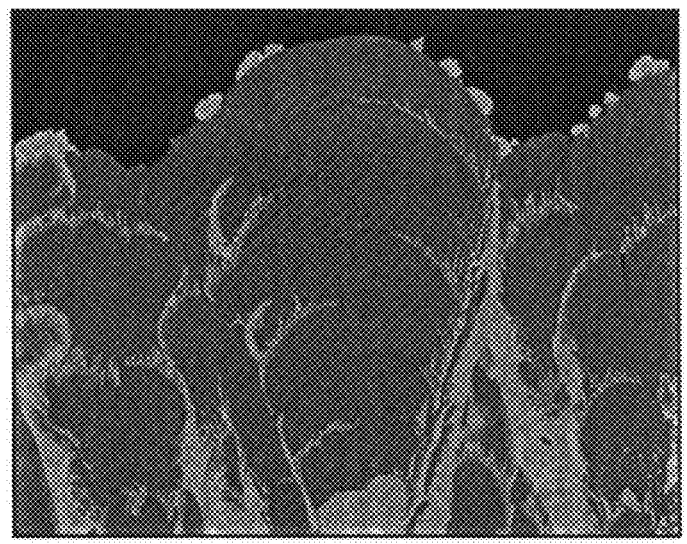
FIGS. 6A and 6B are an SEM photograph showing another cross sectional structure of the anode shown in FIG. 2 and a schematic view thereof.
Figure 6B:
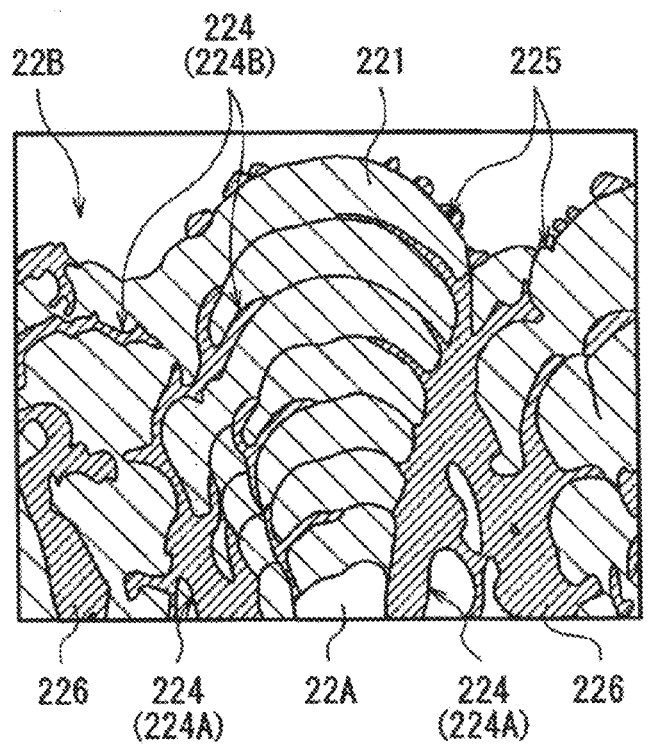

FIGS. 6A and 6B show another cross sectional structure of the anode 22, and correspond to FIGS. 6A and 5B. The anode active material layer 22B has a metal material 226 not being alloyed with the electrode reactant in the gaps 224A and 224B. In this case, only one of the gaps 224A and 224B may have the metal material 226, but the both gaps 224A and 224B preferably have the metal material 226, since thereby higher effect is obtained.

The metal material 226 intrudes into the gap 224A between adjacent anode active material particles 221. More specifically, in the case where the anode active material particles 221 are formed by vapor-phase deposition method or the like, the anode active material particles 221 are grown for every projection existing on the surface of the anode current collector 22A as described above, and thus the gap 224A is generated between the adjacent anode active material particles 221. The gap 224A causes lowering of the binding characteristics of the anode active material layer 22B. Therefore, to improve the binding characteristics, the metal material 226 fills in the foregoing gap 224A. In this case, it is enough that part of the gap 224A is filled therewith, but the larger filling amount is preferable, since thereby the binding characteristics of the anode active material layer 22B are further improved. The filling amount of the metal material 226 is preferably 20% or more, more preferably 40% or more, and much more preferably 80% or more.

Further, the metal material 226 intrudes into the gap 224B in the anode active material particles 221. More specifically, in the case where the anode active material particles 221 have a multilayer structure, the gap 224B is generated between each layer. The gap 224B causes lowering of the binding characteristics of the anode active material layer 22B as the foregoing gap 224A does. Therefore, to improve the binding characteristics, the metal material 226 fills in the foregoing gap 224B. In this case, it is enough that part of the gap 224B is filled therewith, but the larger filling amount is preferable, since thereby the binding characteristics of the anode active material layer 22B are further improved.

To prevent the fibrous minute projection (not shown) generated on the exposed face of the uppermost layer of the anode active material particles 221 from adversely affecting the performance of the secondary battery, the void 225 may have the metal material 226. More specifically, in the case where the anode active material particles 221 are formed by vapor-phase deposition method or the like, the fibrous minute projections are generated on the surface thereof, and thus the void 225 is generated between the projections. The void 225 causes increase of the surface area of the anode active material particles 221, and accordingly the amount of an irreversible coat formed on the surface is also increased, possibly resulting in lowering of progression of the electrode reaction (charge and discharge reaction). Therefore, to avoid the lowering of progression of the electrode reaction, the foregoing void 225 is filled with the metal material 226. In this case, it is enough that part of the void 225 is filled therewith, but the larger filling amount is preferable, since thereby the lowering of progression of the electrode reaction is further suppressed. In FIGS. 6A and 6B, the metal material 226 is dotted on the surface of the uppermost layer of the anode active material particles 221, which means that the foregoing minute projection exists in the location where the metal material 226 is dotted. It is needless to say that the metal material 226 is not necessarily dotted on the surface of the anode active material particles 221, but may cover the entire surface thereof.

In particular, the metal material 226 that intrudes into the gap 224B has a function to fill in the void 225 in each layer. More specifically, in the case where the anode material is deposited several times, the foregoing minute projection is generated on the surface of the anode active material particle 221 for every deposition. Therefore, the metal material 226 fills in not only the gap 224B in each layer, but also the void 225 in each layer.

In FIGS. 5A and 5B and 6A and 6B, the description has been given of a case that the anode active material particles 221 have the multilayer structure, and the both gaps 224A and 224B exist in the anode active material layer 22B. Thus, in this case, the anode active material layer 22B has the metal material 226 in the gaps 224A and 224B. Meanwhile, in the case where the anode active material particles 221 have a single layer structure, and only the gap 224A exists in the anode active material layer 22B, the anode active material layer 22B has the metal material 226 only in the gap 224A. It is needless to say that the void 225 is generated in the both cases, and thus in any case, the metal material 226 is included in the void 225.

The coat 22C contains one or more of the foregoing sulfone compounds. In the case where the coat 22C is provided on the anode active material layer 22B, chemical stability of the anode 22 is improved, and accordingly the chemical stability of the electrolytic solution adjacent to the anode 22 is improved. Thereby, lithium is efficiently inserted in the anode 22 and extracted from the anode 22, and decomposition reaction of the electrolytic solution is prevented. In result, the cycle characteristics are improved.

The coat 22C may be provided to cover the entire face of the anode active material layer 22B, or may be provided to cover part of the surface thereof. In this case, part of the coat 22C may intrude into the anode active material layer 22B.

In particular, the coat 22C preferably contains one or more alkali metal salts or one or more alkali earth metal salts (except for the compounds corresponding to the foregoing sulfone compound) together with the foregoing sulfone compound. Thereby, coat resistance is suppressed, and thus the cycle characteristics are further improved.

As the alkali metal salt or the alkali earth metal salt, for example, a carbonate, a halide salt, a borate, a phosphate, a sulfonate and the like of the alkali metal element or the alkali earth metal element are cited. Specifically, for example, lithium carbonate ($Li_2CO_3$), lithium fluoride (LiF), lithium tetraborate ($Li_2B_4O_7$), lithium metaborate ($LiBO_2$), lithium pyrophosphate ($Li_4P_2O_7$), lithium tripolyphosphate ($Li_5P_3O_{10}$), lithium orthosilicate ($Li_4SiO_4$), lithium metasilicate ($Li_2SiO_3$), dilithium ethanedisulfonate, dilithium propanedifulfonate, dilithium sulfoacetate, dilithium sulfopropionate, dilithium sulfobutanate, dilithium sulfobenzoate, dilithium succinate, trilithium sulfosuccinate, dilithium quadratic acid, magnesium ethanedisulfonate, magnesium propanedisulfonate, magnesium sulfoacetate, magnesium sulfopropionate, magnesium sulfobutanate, magnesium sulfobenzoate, magnesium succinate, trimagnesium disulfosuccinate, calcium ethanedisulfonate, calcium propanedisulfonate, calcium sulfoacetate, calcium sulfopropionate, calcium sulfobutanate, calcium sulfobenzoate, calcium succinate, tricalcium disulfobenzoate and the like are cited.

As a method of forming the coat 22C, for example, liquid-phase deposition method such as coating method, dipping method, and dip coating method; and vapor-phase deposition method such as evaporation method, sputtering method, and Chemical Vapor Deposition (CVD) method are cited. One thereof may be used singly, or two or more methods may be used. Specially, as the liquid-phase deposition method, the coat 22C is preferably formed by using a solution containing the foregoing sulfone compound. Specifically, for example, in the dipping method, the anode current collector 22A on which the anode active material layer 22B is formed is dipped in the solution containing the sulfone compound. In the coating method, the surface of the anode active material layer 22B is coated with the solution containing the sulfone compound. Thereby, the favorable coat 22B having high chemical stability is easily formed. As a solvent in which the sulfone compound is dissolved, for example, a solvent having high polarity such as water is cited.

The separator 23 separates the cathode 21 from the anode 22, and passes lithium ions while preventing current short circuit due to contact of the both electrodes. The separator 23 is made of, for example, a porous film made of a synthetic resin such as polytetrafluoroethylene, polypropylene, and polyethylene, or a ceramic porous film. The separator 23 may have a structure in which two or more porous films as the foregoing porous films are layered.

An electrolytic solution as a liquid electrolyte is impregnated in the separator 23. The electrolytic solution contains a solvent and an electrolyte salt dissolved in the solvent.

The solvent contains, for example, one or more nonaqueous solvents such as an organic solvent. The nonaqueous solvents include, for example, an ester carbonate solvent such as ethylene carbonate, propylene carbonate, butylene carbonate, dimethyl carbonate, diethyl carbonate, ethyl methyl carbonate, and methyl propyl carbonate. Thereby, superior capacity characteristics, superior cycle characteristics, and superior storage characteristics are obtained. Specially, a mixture of a high viscosity solvent such as ethylene carbonate and propylene carbonate and a low viscosity solvent such as dimethyl carbonate, ethyl methyl carbonate, and diethyl carbonate is preferable. Thereby, the dissociation characteristics of the electrolyte salt and the ion mobility are improved, and thus higher effect is obtained.

The solvent preferably contains a cyclic ester carbonate having an unsaturated bond shown in Chemical formula 11 to Chemical formula 13. Thereby, the cycle characteristics are improved. One thereof may be used singly, or a plurality thereof may be used by mixture.

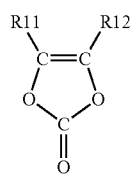

Chemical formula 11

R11 and R12 are a hydrogen group or an alkyl group.

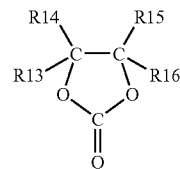

Chemical formula 12

R13 to R16 are a hydrogen group, an alkyl group, a vinyl group, or an aryl group. At least one of R13 to R16 is the vinyl group or the aryl group.

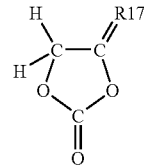

Chemical formula 13

R17 is an alkylene group.

The cyclic ester carbonate having an unsaturated bond shown in Chemical formula 11 is a vinylene carbonate-based compound. As the vinylene carbonate-based compound, for example, vinylene carbonate (1,3-dioxole-2-one), methylvinylene carbonate (4-methyl-1,3-dioxole-2-one), ethylvinylene carbonate (4-ethyl-1,3-dioxole-2-one), 4,5-dimethyl-1,3-dioxole-2-one, 4,5-diethyl-1,3-dioxole-2-one, 4-fluoro-1,3-dioxole-2-one, 4-trifluoromethyl-1,3-dioxole-2-one and the like are cited. Specially, vinylene carbonate is preferable, since vinylene carbonate is easily available, and provides high effect.

The cyclic ester carbonate having an unsaturated bond shown in Chemical formula 12 is a vinylethylene carbonate-based compound. As the vinylethylene carbonate-based compound, for example, vinylethylene carbonate (4-vinyl-1,3-dioxolane-2-one), 4-methyl-4-vinyl-1,3-dioxolane-2-one, 4-ethyl-4-vinyl-1,3-dioxolane-2-one, 4-n-propyl-4-vinyl-1,3-dioxolane-2-one, 5-methyl-4-vinyl-1,3-dioxolane-2-one, 4,4-divinyl-1,3-dioxolane-2-one, 4,5-divinyl-1,3-dioxolane-2-one and the like are cited. Specially, vinylethylene carbonate is preferable, since vinylethylene carbonate is easily available, and provides high effect. It is needless to say that all of R13 to R16 may be the vinyl group or the aryl group. Otherwise, it is possible that some of R13 to R16 are the vinyl group, and the others thereof are the aryl group.

The cyclic ester carbonate having an unsaturated bond shown in Chemical formula 13 is a methylene ethylene carbonate-based compound. As the methylene ethylene carbonate-based compound, 4-methylene-1,3-dioxolane-2-one, 4,4-dimethyl-5-methylene-1,3-dioxolane-2-one, 4,4-diethyl-5-methylene-1,3-dioxolane-2-one and the like are cited. The methylene ethylene carbonate compound may have one methylene group (compound shown in Chemical formula 13), or have two methylene groups.

The cyclic ester carbonate having an unsaturated bond may be catechol carbonate having a benzene ring or the like, in addition to the compounds shown in Chemical formula 11 to Chemical formula 13.

The solvent preferably contains at least one of a chain ester carbonate having halogen as an element shown in Chemical formula 14 and a cyclic ester carbonate having halogen as an element shown in Chemical formula 15. Thereby, a stable protective film is formed on the surface of the anode 22 and decomposition reaction of the electrolytic solution is prevented, and thus the cycle characteristics are improved.

Chemcial formula 14

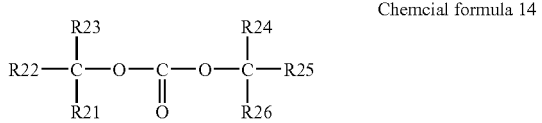

R21 to R26 are a hydrogen group, a halogen group, an alkyl group, or an alkyl halide group. At least one of R21 to R26 is the halogen group or the alkyl halide group.

Chemical formula 15

R27 to R30 are a hydrogen group, a halogen group, an alkyl group, or an alkyl halide group. At least one of R27 to R30 is the halogen group or the alkyl halide group.

R21 to R26 in Chemical formula 14 may be identical or different. The same is applied to R27 to R30 in Chemical formula 15. The halogen type is not particularly limited, but for example, at least one selected from the group consisting of fluorine, chlorine, and bromine is cited. Specially, fluorine is preferable, since thereby higher effect is obtained. It is needless to say that other halogen may be used.

The number of halogen is more preferably two than one, and further may be three or more, since thereby an ability to form the protective film becomes high, and more rigid and stable protective film is formed. Accordingly, decomposition reaction of the electrolytic solution is further suppressed.

As the chain ester carbonate having halogen shown in Chemical formula 14, for example, fluoromethyl methyl carbonate, bis(fluoromethyl) carbonate, difluoromethyl methyl carbonate and the like are cited. One thereof may be used singly, or a plurality thereof may be used by mixture.

As the cyclic ester carbonate having halogen shown in Chemical formula 15, for example, the compounds shown in Chemical formulas 16 and 17 are cited. That is, 4-fluoro-1,3-dioxolane-2-one of Chemical formula 16(1), 4-chloro-1,3-dioxolane-2-one of Chemical formula 16(2), 4,5-difluoro-1,3-dioxolane-2-one of Chemical formula 16(3), tetrafluoro-1,3-dioxolane-2-one of Chemical formula 16(4), 4-fluoro-5-chloro-1,3-dioxolane-2-one of Chemical formula 16(5), 4,5-dichloro-1,3-dioxolane-2-one of Chemical formula 16(6), tetrachloro-1,3-dioxolane-2-one of Chemical formula 16(7), 4,5-bistrifluoro methyl-1,3-dioxolane-2-one of Chemical formula 16(8), 4-trifluoro methyl-1,3-dioxolane-2-one of Chemical formula 16(9), 4,5-difluoro-4,5-dimethyl-1,3-dioxolane-2-one of Chemical formula 16(10), 4-methyl-5,5-difluoro-1,3-dioxolane-2-one of Chemical formula 16(11), 4-ethyl-5,5-difluoro-1,3-dioxolane-2-one of Chemical formula 16(12) and the like are cited. Further, 4-trifluoromethyl-5-fluoro-1,3-dioxolane-2-one of Chemical formula 17(1), 4-trifluoromethyl-5-methyl-1,3-dioxolane-2-one of Chemical formula 17(2), 4-fluoro-4,5-dimethyl-1,3-dioxolane-2-one of Chemical formula 17(3), 4,4-difluoro-5-(1,1-difluoroethyl)-1,3-dioxolane-2-one of Chemical formula 17(4), 4,5-dichloro-4,5-dimethyl-1,3-dioxolane-2-one of Chemical formula 17(5), 4-ethyl-5-fluoro-1,3-dioxolane-2-one of Chemical formula 17(6), 4-ethyl-4,5-difluoro-1,3-dioxolane-2-one of Chemical formula 17(7), 4-ethyl-4,5,5-trifluoro-1,3-dioxolane-2-one of Chemical formula 17(8), 4-fluoro-4-methyl-1,3-dioxolane-2-one of Chemical formula 17(9) and the like are cited. One thereof may be used singly, or a plurality thereof may be used by mixture.

Chemical formula 16

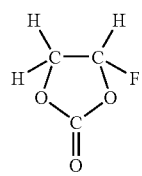 (1)

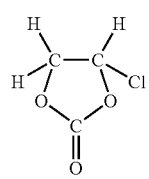 (2)

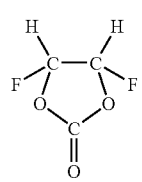 (3)

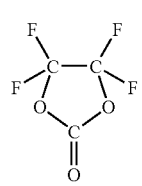 (4)

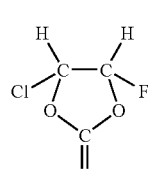 (5)

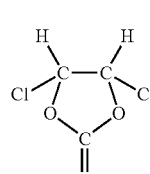 (6)

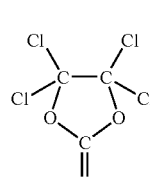 (7)

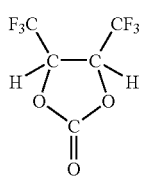
(8)

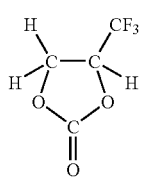
(9)

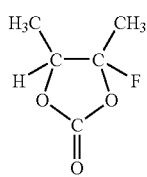
(10)

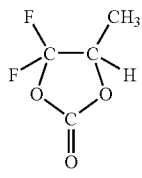
(11)

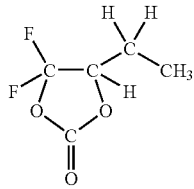
(12)

Chemical formula 17

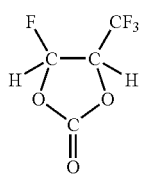
(1)

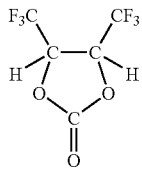
(2)

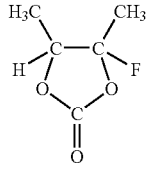
(3)

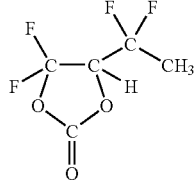
(4)

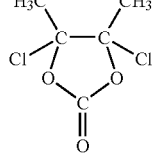
(5)

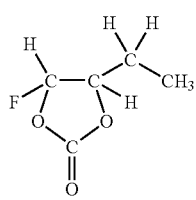
(6)

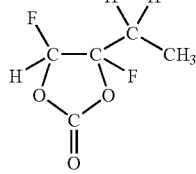
(7)

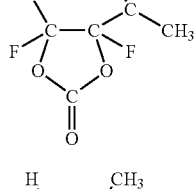
(8)

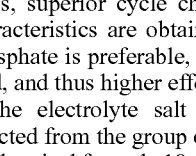
(9)

Specially, 4-fluoro-1,3-dioxolane-2-one or 4,5-difluoro-1,3-dioxolane-2-one is preferable, and 4,5-difluoro-1,3-dioxolane-2-one is more preferable. In particular, as 4,5-difluoro-1,3-dioxolane-2-one, a trans isomer is preferable to a cis isomer, since the trans isomer is easily available and provides high effect.

The electrolyte salt contains, for example, one or more light metal salts such as a lithium salt. As the lithium salt, for example, lithium hexafluorophosphate, lithium tetrafluoroborate, lithium perchlorate, lithium hexafluoroarsenate and the like are cited, since thereby superior capacity characteristics, superior cycle characteristics, and superior storage characteristics are obtained. Specially, lithium hexafluorophosphate is preferable, since the internal resistance is lowered, and thus higher effect is obtained.

The electrolyte salt preferably contains at least one selected from the group consisting of the compounds shown in Chemical formula 18 to Chemical formula 20. Thereby, in the case where such a compound is used together with the foregoing lithium hexafluorophosphate or the like, higher effect is obtained. R33 in Chemical formula 18 may be identical or different. The same is applied to R41 to R43 in Chemical formula 19 and R51 and R52 in Chemical formula 20.

Chemical formula 18

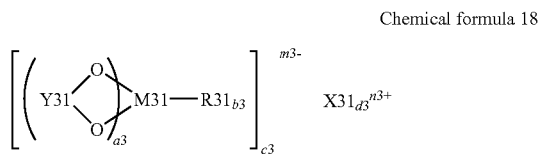

X31 is a Group 1 element or a Group 2 element in the long period periodic table or aluminum. M31 is a transition metal, a Group 13 element, a Group 14 element, or a Group 15 element in the long period periodic table. R31 is a halogen group. Y31 is —OC—R32-CO—, —OC—C(R33)$_2$-, or —OC—CO—. R32 is an alkylene group, an alkylene halide group, an arylene group, or an arylene halide group. R33 is an alkyl group, an alkyl halide group, an aryl group, or an aryl halide group. a3 is one of integer numbers 1 to 4. b3 is one of integer numbers 0, 2, and 4. c3, d3, m3, and n3 are one of integer numbers 1 to 3.

Chemical formula 19

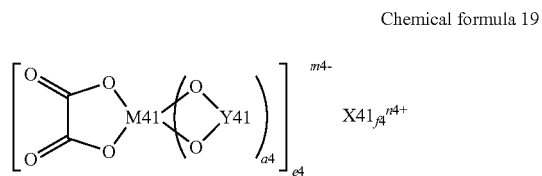

X41 is a Group 1 element or a Group 2 element in the long period periodic table. M41 is a transition metal, a Group 13 element, a Group 14 element, or a Group 15 element in the long period periodic table. Y41 is —OC—(C(R41)$_2$)$_{b4}$-CO—, —(R43)$_2$C—(C(R42)$_2$)$_{c4}$-CO—, —(R43)$_2$C—(C(R42)$_2$)$_{c4}$-C(R43)$_2$-, —(R43)$_2$C—(C(R42)$_2$)$_{c4}$-SO$_2$—, —O$_2$S—(C(R42)$_2$)$_{d4}$-SO$_2$—, or —OC—(C(R42)$_2$)$_{d4}$-SO$_2$—. R41 and R43 are a hydrogen group, an alkyl group, a halogen group, or an alkyl halide group. At least one of R41 and R43 is respectively the halogen group or the alkyl halide group. R42 is a hydrogen group, an alkyl group, a halogen group, or an alkyl halide group. a4, e4, and n4 are an integer number of 1 or 2. b4 and d4 are one of integer numbers 1 to 4. c4 is one of integer numbers 0 to 4. f4 and m4 are one of integer numbers 1 to 3.

Chemical formula 20

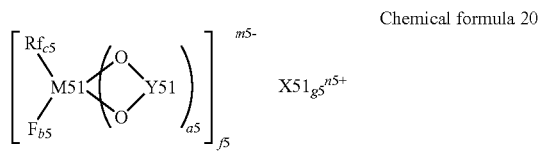

X51 is a Group 1 element or a Group 2 element in the long period periodic table. M51 is a transition metal element, a Group 13 element, a Group 14 element, or a Group 15 element in the long period periodic table. Rf is a fluorinated alkyl group with the carbon number in the range from 1 to 10 or a fluorinated aryl group with the carbon number in the range from 1 to 10. Y51 is —OC—(C(R51)$_2$)$_{d5}$-CO—, —(R52)$_2$C—(C(R51)$_2$)$_{d5}$-CO—, —(R52)$_2$C—(C(R51)$_2$)$_{d5}$-C(R52)$_2$—, —(R52)$_2$C—(C(R51)$_2$)$_{d5}$-SO$_2$—, —O$_2$S—(C(R51)$_2$)$_{e5}$-SO$_2$—, or —OC—(C(R51)$_2$)$_{e5}$-SO$_2$—. R51 is a hydrogen group, an alkyl group, a halogen group, or an alkyl halide group. R52 is a hydrogen group, an alkyl group, a halogen group, or an alkyl halide group, and at least one thereof is the halogen group or the alkyl halide group. a5, f5, and n5 are an integer number of 1 or 2. b5, c5, and e5 are one of integer numbers 1 to 4. d5 is one of integer numbers 0 to 4. g5 and m5 are one of integer numbers 1 to 3.

The long period periodic table is shown in "Inorganic chemistry nomenclature (revised edition)" proposed by IUPAC (International Union of Pure and Applied Chemistry). Specifically, Group 1 element represents hydrogen, lithium, sodium, potassium, rubidium, cesium, and francium. Group 2 element represents beryllium, magnesium, calcium, strontium, barium, and radium. Group 13 element represents boron, aluminum, gallium, indium, and thallium. Group 14 element represents carbon, silicon, germanium, tin, and lead. Group 15 element represents nitrogen, phosphorus, arsenic, antimony, and bismuth.

As a compound shown in Chemical formula 18, for example, the compounds shown in Chemical formula 21 and the like are cited. As a compound shown in Chemical formula 19, for example, the compounds shown in Chemical formula 22 and the like are cited. As a compound shown in Chemical formula 20, for example, the compound shown in Chemical formula 23 and the like are cited. It is needless to say that the compound is not limited to the compounds shown in Chemical formula 21-1 to Chemical formula 23, and the compound may be other compound as long as such a compound has the structure shown in Chemical formula 18 to Chemical formula 20.

Chemical formula 21

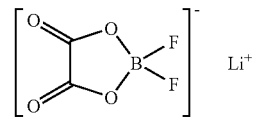 (1)

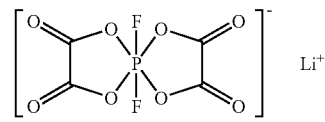 (2)

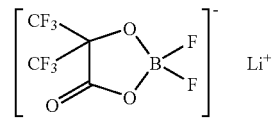 (3)

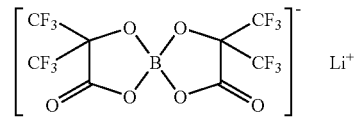 (4)

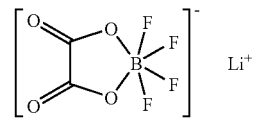 (5)

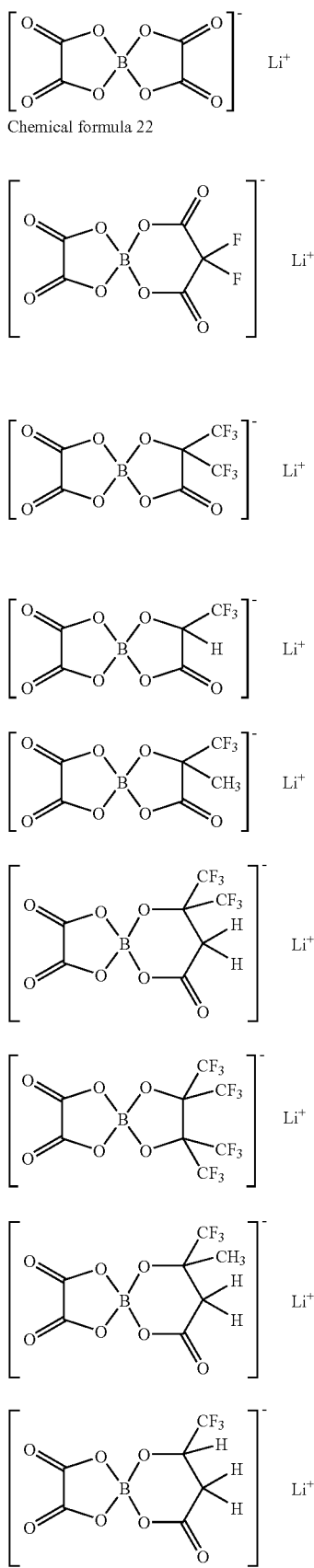

Further, the electrolyte salt may contain at least one selected from the group consisting of the compounds shown in Chemical formula 24 to Chemical formula 26. Thereby, in the case where such a compound is used together with the foregoing lithium hexafluorophosphate or the like, higher effect is obtained. m and n in Chemical formula 24 may be identical or different. The same is applied to p, q, and r in Chemical formula 26.

$$LiN(C_mF_{2m+1}SO_2)(C_nF_{2n+1}SO_2) \qquad \text{Chemical formula 24}$$

m and n are an integer number of 1 or more.

Chemical formula 25

R61 is a straight chain or branched perfluoro alkylene group with the carbon number in the range from 2 to 4, both inclusive.

$$LiC(C_pF_{2p+1}SO_2)(C_qF_{2q+1}SO_2)(C_rF_{2r+1}SO_2) \qquad \text{Chemical formula 26}$$

p, q, and r are an integer number of 1 or more.

As the chain compound shown in Chemical formula 24, for example, lithium bis(trifluoromethanesulfonyl)imideo (LiN(CF$_3$SO$_2$)$_2$), lithium bis(pentafluoroethanesulfonyl)imide (LiN(C$_2$F$_5$SO$_2$)$_2$), lithium (trifluoromethanesulfonyl)(pentafluoroethanesulfonyl)imide (LiN(CF$_3$SO$_2$)(C$_2$F$_5$SO$_2$)), lithium(trifluoromethanesulfonyl)(heptafluoropropanesulfonyl)imide (LiN(CF$_3$SO$_2$)(C$_3$F$_7$SO$_2$)), lithium(trifluoromethanesulfonyl)(nonafluorobutanesulfonyl)imide (LiN(CF$_3$SO$_2$)(C$_4$F$_9$SO$_2$)) and the like are cited. One thereof may be used singly, or a plurality thereof may be used by mixture.

As the cyclic compound shown in Chemical formula 25, for example, the compounds shown in Chemical formula 27 are cited. That is, lithium 1,2-perfluoroethanedisulfonylimide shown in Chemical formula 27(1), lithium 1,3-perfluoropropanedisulfonylimide shown in Chemical formula 27(2), lithium 1,3-perfluorobutanedisulfonylimide shown in Chemical formula 27(3), lithium 1,4-perfluorobutanedisulfonylimide shown in Chemical formula 27(4) and the like are cited. One thereof may be used singly, or a plurality thereof may be used by mixture. Specially, lithium 1,2-perfluoroethanedisulfonylimide is preferable, since thereby high effect is obtained.

Chemical formula 27

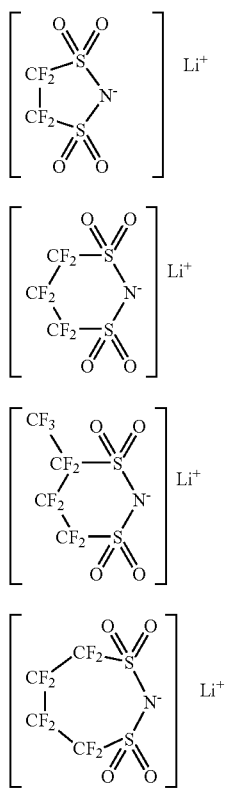

As the chain compound shown in Chemical formula 26, for example, lithium tris(trifluoromethanesulfonyl)methyde (LiC(CF$_3$SO$_2$)$_3$) and the like are cited.

The content of the electrolyte salt to the solvent is preferably in the range from 0.3 mol/kg to 3.0 mol/kg, both inclusive. If the content is out of the foregoing range, there is a possibility that the ion conductivity is significantly lowered.

The electrolytic solution may contain various additives together with the solvent and the electrolyte salt, since thereby chemical stability of the electrolytic solution is further improved.

As the additive, for example, sultone (cyclic sulfonic ester) is cited. The sultone is, for example, propane sultone, propene sultone or the like. Specially, propene sultone is preferable. Such sultone may be used singly, or a plurality thereof may be used by mixture. The sultone content in the electrolytic solution is, for example, in the range from 0.5 wt % to 5 wt %, both inclusive.

Further, as the additive, for example, an acid anhydride is cited. The acid anhydride is, for example, a carboxylic anhydride such as succinic anhydride, glutaric anhydride, and maleic anhydride; a disulfonic anhydride such as ethane disulfonic anhydride and propane disulfonic anhydride; an anhydride of carboxylic acid and sulfonic acid such as sulfobenzoic anhydride, sulfopropionic anhydride, and sulfobutyric anhydride or the like. Specially, succinic anhydride or sulfobenzoic anhydride is preferable. The anhydrides may be used singly, or a plurality thereof may be used by mixture. The content of the acid anhydride in the electrolytic solution is, for example, in the range from 0.5 wt % to 5 wt %, both inclusive.

The secondary battery is manufactured, for example, by the following procedure.

First, the cathode 21 is formed. First, a cathode active material, a binder, and an electrical conductor are mixed to prepare a cathode mixture, which is dispersed in an organic solvent to form paste cathode mixture slurry. Subsequently, the both faces of the cathode current collector 21A are uniformly coated with the cathode mixture slurry by a doctor blade, a bar coater or the like, which is dried. Finally, the coating is compression-molded by a rolling press machine or the like while being heated if necessary to form the cathode active material layer 21B. In this case, the coating may be compression-molded over several times.

Next, the anode 22 is formed. First, the anode current collector 22A made of an electrolytic copper foil or the like is prepared. After that, the anode material is deposited on the both faces of the anode current collector 22A by vapor-phase deposition method such as evaporation method to form the plurality of anode active material particles. Subsequently, if necessary, the oxide-containing film is formed by liquid-phase method such as liquid-phase precipitation method, or the metal material is formed by liquid-phase deposition method such as electrolytic plating method to form the anode active material layer 22B. Subsequently, as a solution containing the foregoing sulfone compound, for example, an aqueous solution with a concentration in the range from 1 wt % to 5 wt %, both inclusive is prepared. Finally, the anode current collector 22A on which the anode active material layer 22B is formed is dipped in a solution for several seconds and taken out. The resultant is dried at room temperature to form the coat 22C. In forming the coat 22C, it is possible that the surface of the anode active material layer 22B is coated with the foregoing solution and then the resultant is dried.

Next, the cathode lead 25 is attached to the cathode current collector 21A by welding or the like, and the anode lead 26 is attached to the anode current collector 22A by welding or the like. After that, the cathode 21 and the anode 22 are layered with the separator 23 in between, and spirally wound in the longitudinal direction to form the spirally wound electrode body 20.

The secondary battery is assembled as follows. First, an end of the cathode lead 25 is welded to the safety valve mechanism 15, and an end of the anode lead 26 is welded to the battery can 11. Subsequently, while the spirally wound electrode body 20 is sandwiched between the pair of insulating plates 12 and 13, the spirally wound electrode body 20 is contained in the battery can 11. Subsequently, the electrolytic solution is injected into the battery can 11, and impregnated in the separator 23. Finally, the battery cover 14, the safety valve mechanism 15, and the PTC device 16 are fixed at the open end of the battery can 11 by being caulked with the gasket 17. Accordingly, the secondary battery shown in FIG. 1 and FIG. 2 is thereby completed.

In the secondary battery, when charged, for example, lithium ions are extracted from the cathode 21, and are inserted in the anode 22 through the electrolytic solution impregnated in the separator 23. Meanwhile, when discharged, for example, lithium ions are extracted from the anode 22, and are inserted in the cathode 21 through the electrolytic solution impregnated in the separator 23.

In the cylindrical secondary battery, since the anode 22 has the structure similar to that of the foregoing anode, chemical stability of the anode 22 is improved. Thereby, lithium ions are easily inserted into the anode 22 and extracted from the anode 22, and decomposition reaction of the electrolytic solution is suppressed. Accordingly, the cycle characteristics are able to be improved. In this case, the coat 22C is formed by using the solution containing the foregoing sulfone compound. Specifically, the simple treatment such as dipping treatment and coating treatment is used. Therefore, compared to a case using a method necessitating special environmental conditions such as reduced pressure environment, the favorable coat 22C is able to be formed easily.

In particular, in the case where the anode 22 contains silicon or the like advantageous to realizing a high capacity (material that is able to insert and extract lithium and that has at least one of a metal element and a metalloid element), the cycle characteristics are improved. Thus, in this case, higher effect is able to be obtained than in the case where the anode 22 contains other anode material such as a carbon material.

Second Secondary Battery

Figure 7:
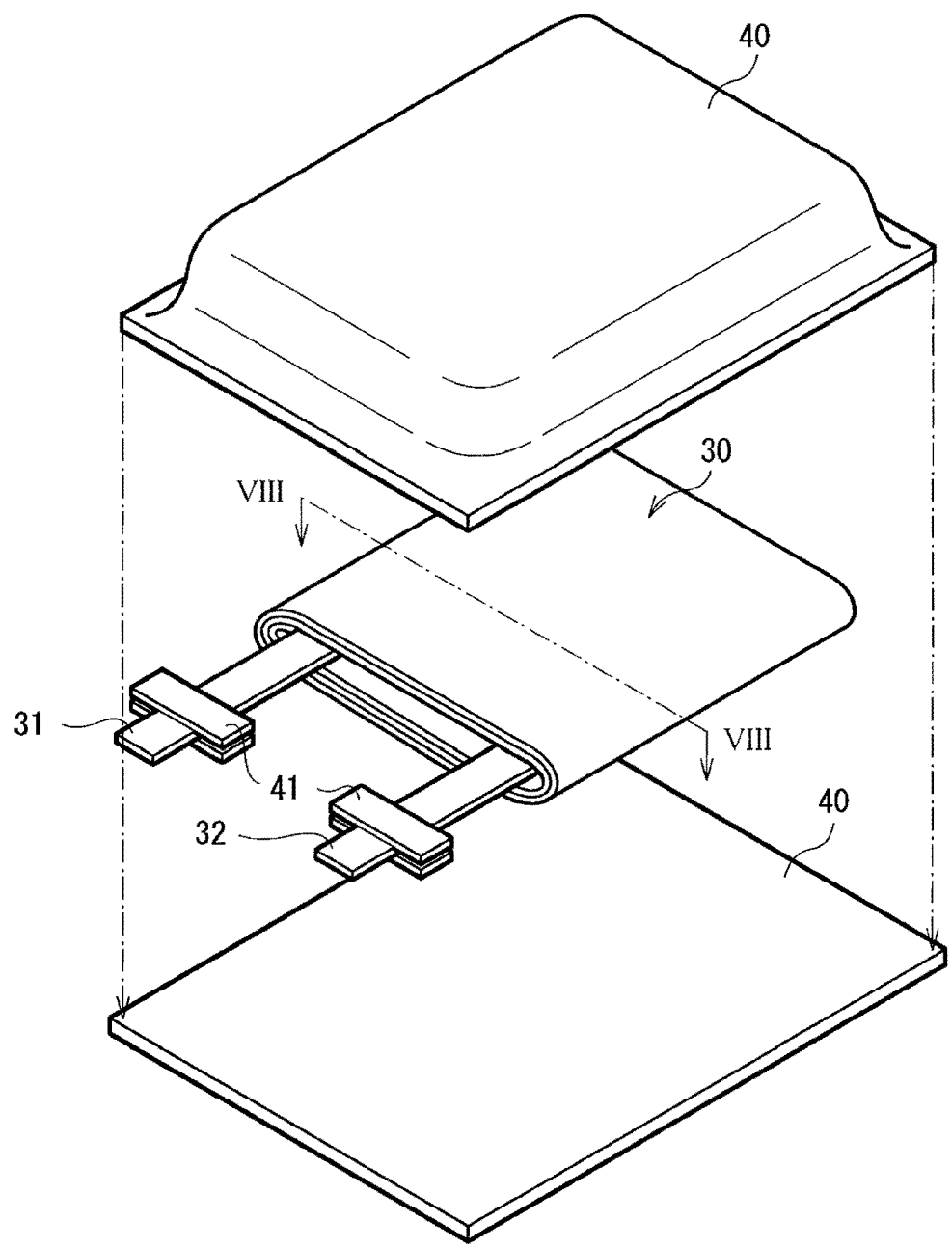
FIG. 7 is a cross sectional view showing a structure of a second secondary battery using the sulfone compound according to the embodiment of the invention.
Figure 8:
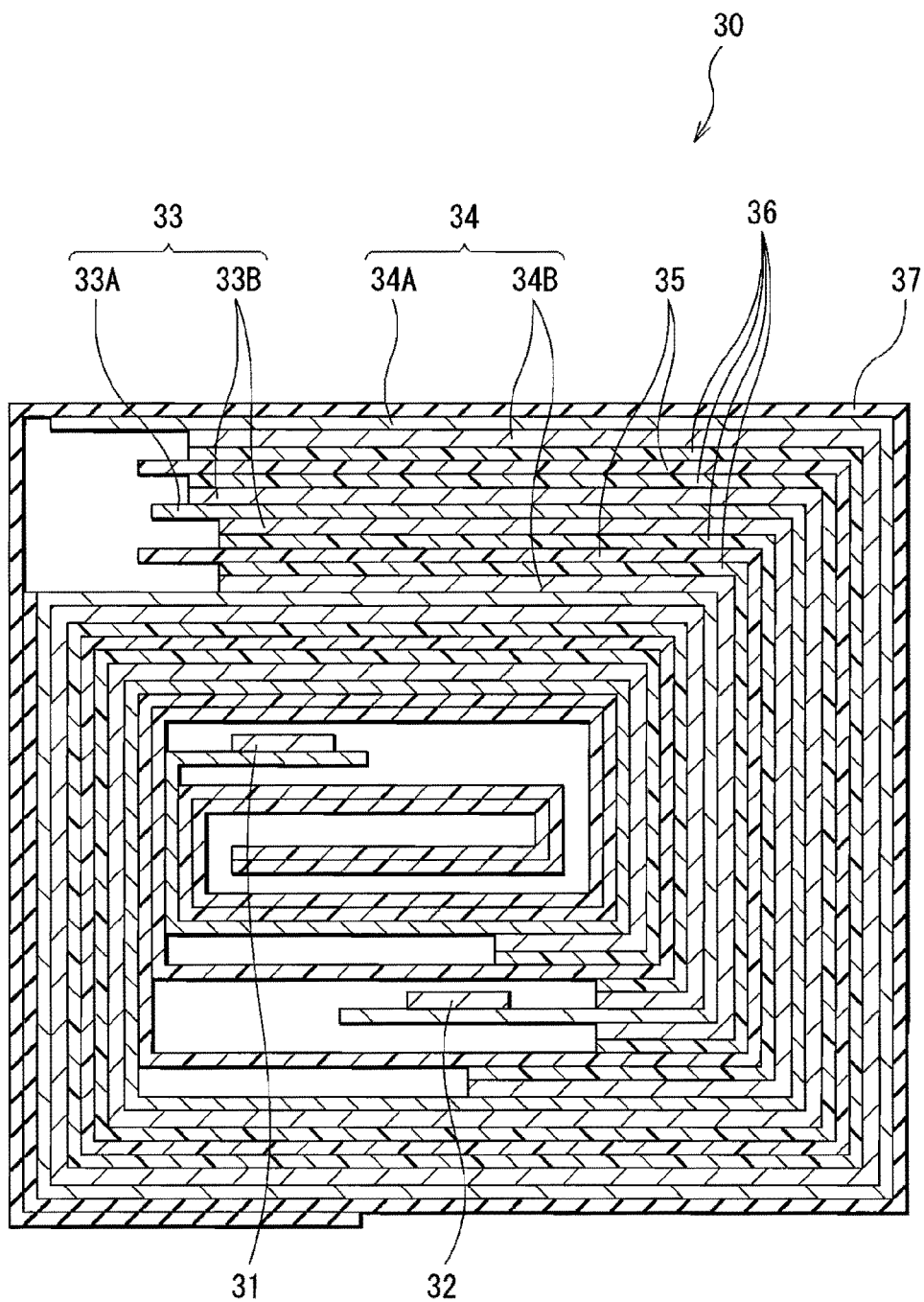
FIG. 8 is a cross sectional view taken along line VIII-VIII of the spirally wound electrode body shown in FIG. 7.

FIG. 7 shows an exploded perspective structure of a second secondary battery. FIG. 8 shows an enlarged cross section taken along line VIII-VIII of a spirally wound electrode body 30 shown in FIG. 7.

The secondary battery is, for example, a lithium ion secondary battery similar to the foregoing first secondary battery. In the secondary battery, the spirally wound electrode body 30 on which a cathode lead 31 and an anode lead 32 are attached is contained in a film package member 40. The battery structure including the film package member 40 is called laminated film structure.

The cathode lead 31 and the anode lead 32 are respectively directed from inside to outside of the package member 40 in the same direction, for example. The cathode lead 31 is made of, for example, a metal material such as aluminum, and the anode lead 32 is made of, for example, a metal material such as copper, nickel, and stainless. The metal materials are in the shape of a thin plate or mesh.

The package member 40 is made of an aluminum laminated film in which, for example, a nylon film, an aluminum foil, and a polyethylene film are bonded together in this order. The package member 40 has, for example, a structure in which the respective outer edges of two pieces of rectangle aluminum laminated films are bonded to each other by fusion bonding or an adhesive so that the polyethylene film and the spirally wound electrode body 30 are opposed to each other.

An adhesive film 41 to protect from entering of outside air is inserted between the package member 40 and the cathode lead 31, the anode lead 32. The adhesive film 41 is made of a material having contact characteristics to the cathode lead 31 and the anode lead 32. Examples of such a material include, for example, a polyolefin resin such as polyethylene, polypropylene, modified polyethylene, and modified polypropylene.

The package member 40 may be made of a laminated film having other lamination structure, a polymer film such as polypropylene, or a metal film, instead of the foregoing aluminum laminated film.

In the spirally wound electrode body 30, a cathode 33 and an anode 34 are layered with a separator 35 and an electrolyte 36 in between and then spirally wound. The outermost periphery thereof is protected by a protective tape 37.

Figure 9:
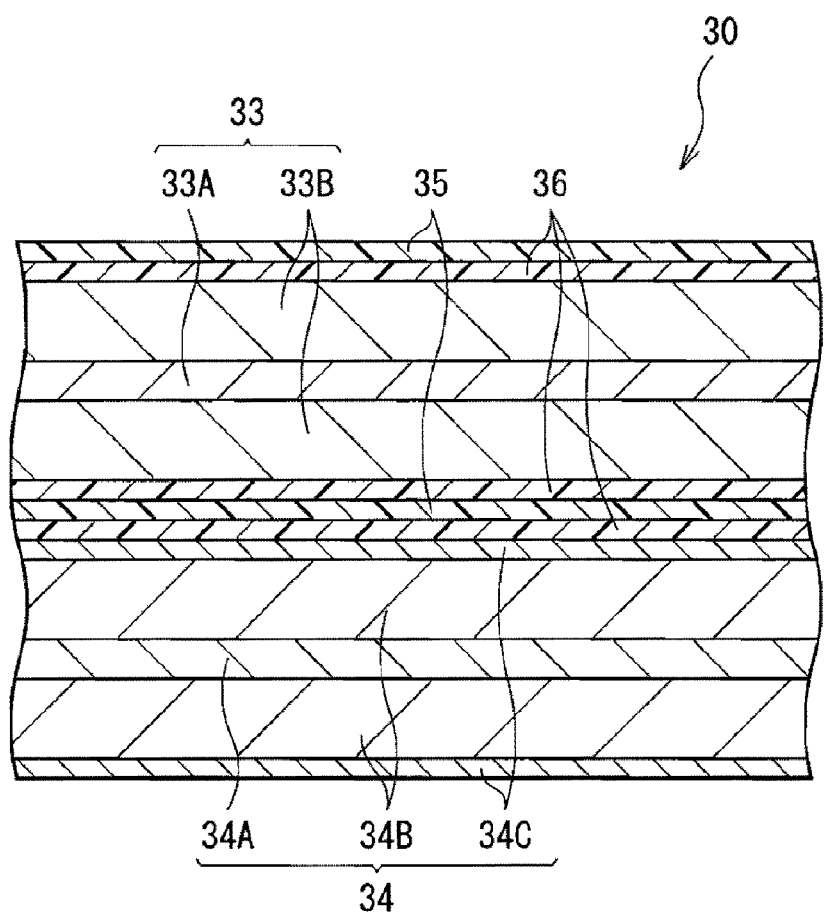
FIG. 9 is a cross sectional view showing an enlarged part of the spirally wound electrode body shown in FIG. 8.

FIG. 9 shows an enlarged part of the spirally wound electrode body 30 shown in FIG. 8. The cathode 33 has a structure in which, for example, a cathode active material layer 33B is provided on the both faces of a cathode current collector 33A having a pair of faces. The anode 34 has, for example, a structure in which an anode active material layer 34B and a coat 34C are provided on the both faces of an anode current collector 34A having a pair of faces. The structures of the cathode current collector 33A, the cathode active material layer 33B, the anode current collector 34A, the anode active material layer 34B, the coat 34C, and the separator 35 are respectively similar to those of the cathode current collector 21A, the cathode active material layer 21B, the anode current collector 22A, the anode active material layer 22B, the coat 22C, and the separator 23 of the foregoing first secondary battery.

The electrolyte 36 is a so-called gelatinous electrolyte, containing an electrolytic solution and a polymer compound that holds the electrolytic solution. The gelatinous electrolyte is preferable, since thereby high ion conductivity (for example, 1 mS/cm or more at room temperature) is obtained and liquid leakage is prevented.

As the polymer compound, for example, polyacrylonitrile, polyvinylidene fluoride, a copolymer of polyvinylidene fluoride and polyhexafluoro propylene, polytetrafluoroethylene, polyhexafluoro propylene, polyethylene oxide, polypropylene oxide, polyphosphazene, polysiloxane, polyvinyl acetate, polyvinyl alcohol, polymethacrylic acid methyl, polyacrylic acid, polymethacrylic acid, styrene-butadiene rubber, nitrile-butadiene rubber, polystyrene, polycarbonate and the like are cited. One of these polymer compounds may be used singly, or a plurality thereof may be used by mixture. Specially, as a polymer compound, polyacrylonitrile, polyvinylidene fluoride, polyhexafluoro propylene, polyethylene oxide and the like are preferably used, since such a compound is electrochemically stable.

The composition of the electrolytic solution is similar to the composition of the electrolytic solution in the first secondary battery. However, in this case, the solvent means a wide concept including not only the liquid solvent but also a solvent having ion conductivity capable of dissociating the electrolyte salt. Therefore, in the case where the polymer compound having ion conductivity is used, the polymer compound is also included in the solvent.

Instead of the gelatinous electrolyte 36 in which the electrolytic solution is held by the polymer compound, the electrolytic solution may be directly used. In this case, the electrolytic solution is impregnated in the separator 35.

The secondary battery including the gelatinous electrolyte 36 is manufactured, for example, by the following three manufacturing methods.

In the first manufacturing method, first, for example, the cathode 33 is formed by forming the cathode active material layer 33B on the both faces of the cathode current collector 33A, and the anode 34 is formed by forming the anode active material layer 34B and the coat 34C on the both faces of the anode current collector 34A by a procedure similar to the procedure of forming the cathode 21 and the anode 22 in the foregoing first secondary battery. Subsequently, a precursor solution containing an electrolytic solution, a polymer compound, and a solvent is prepared. After the cathode 33 and the anode 34 are coated with the precursor solution, the solvent is volatilized to form the gelatinous electrolyte 36. Subsequently, the cathode lead 31 is attached to the cathode current collector 33A, and the anode lead 32 is attached to the anode current collector 34A. Subsequently, the cathode 33 and the anode 34 provided with the electrolyte 36 are layered with the separator 35 in between to obtain a laminated body. After that, the laminated body is spirally wound in the longitudinal direction, the protective tape 37 is adhered to the outermost periphery thereof to form the spirally wound electrode body 30. Finally, for example, after the spirally wound electrode body 30 is sandwiched between two pieces of the film package members 40, outer edges of the package members 40 are contacted by thermal fusion bonding or the like to enclose the spirally wound electrode body 30. At this time, the adhesive films 41 are inserted between the cathode lead 31, the anode lead 32 and the package member 40. Thereby, the secondary battery shown in FIG. 7 to FIG. 9 is completed.

In the second manufacturing method, first, the cathode lead 31 is attached to the cathode 33, and the anode lead 32 is attached to the anode 34. After that, the cathode 33 and the anode 34 are layered with the separator 35 in between and spirally wound. The protective tape 37 is adhered to the outermost periphery thereof, and thereby a spirally wound body as a precursor of the spirally wound electrode body 30 is formed. Subsequently, after the spirally wound body is sandwiched between two pieces of the film package members 40, the outermost peripheries except for one side are bonded by thermal fusion bonding or the like to obtain a pouched state, and the spirally wound body is contained in the pouch-like package member 40. Subsequently, a composition of matter for electrolyte containing an electrolytic solution, a monomer as a raw material for the polymer compound, a polymerization initiator, and if necessary other material such as a polymerization inhibitor is prepared, which is injected into the pouch-like package member 40. After that, the opening of the package member 40 is hermetically sealed by thermal fusion bonding or the like. Finally, the monomer is thermally polymerized to obtain a polymer compound. Thereby, the gelatinous electrolyte 36 is formed. Accordingly, the secondary battery is completed.

In the third manufacturing method, the spirally wound body is formed and contained in the pouch-like package member 40 in the same manner as that of the foregoing second manufacturing method, except that the separator 35 with the both faces coated with a polymer compound is used firstly. As the polymer compound with which the separator 35 is coated, for example, a polymer containing vinylidene fluoride as a component, that is, a homopolymer, a copolymer, a multicomponent copolymer and the like are cited. Specifically, polyvinylidene fluoride, a binary copolymer containing vinylidene fluoride and hexafluoro propylene as a component, a ternary copolymer containing vinylidene fluoride, hexafluoro propylene, and chlorotrifluoroethylene as a component and the like are cited. As a polymer compound, in addition to the foregoing polymer containing vinylidene fluoride as a component, another one or more polymer compounds may be contained. Subsequently, an electrolytic solution is prepared and injected into the package member 40. After that, the opening of the package member 40 is sealed by thermal fusion bonding or the like. Finally, the resultant is heated while a weight is applied to the package member 40, and the separator 35 is contacted with the cathode 33 and the anode 34 with the polymer compound in between. Thereby, the electrolytic solution is impregnated into the polymer compound, and the polymer compound is gelated to form the electrolyte 36. Accordingly, the secondary battery is completed.

In the third manufacturing method, the swollenness of the secondary battery is suppressed compared to the first manufacturing method. Further, in the third manufacturing method, the monomer, the solvent and the like as a raw material of the polymer compound are hardly left in the electrolyte 36 compared to the second manufacturing method, and the formation step of the polymer compound is favorably controlled. Thus, sufficient contact characteristics are obtained between the cathode 33/the anode 34/the separator 35 and the electrolyte 36.

In the laminated film secondary battery, the anode 34 has a structure similar to that of the foregoing anode. Thus, the cycle characteristics are able to be improved. Effect of the secondary battery other than the foregoing effect is similar to that of the first secondary battery.

EXAMPLES

Examples of the invention will be described in detail.

First, as a representative of the sulfone compounds having a carbonate group and a sulfonyl group of the invention, the sulfone compound shown in Chemical formula 9(1) was synthesized by the following procedure. First, 6.1 g of 4-chloro-1,3-dioxolane-2-one was dissolved in 20 cm$^3$ (20 mL) of deaerated water to prepare an aqueous solution, which was cooled down to 10 deg C. Subsequently, 6.0 g of lithium sulfite was slowly added to the aqueous solution while being agitated. After that, the resultant was agitated for three hours while temperature was gradually increased to room temperature to initiate reaction. Subsequently, the aqueous solution after reaction was screened to remove waste. After that, the aqueous solution was set under the reduced pressure to concentrate a solid as a reactant. Subsequently, the solid as a reactant was added into 50 cm$^3$ (50 mL) of tetrahydrofuran, and the resultant was extracted. The extraction liquid was separated into two layers. Finally, the lower layer of the extraction liquid was dried under the reduced pressure at 110 deg C. to obtain 0.6 g of a colorless compound.

The obtained compound was identified by Nuclear Magnetic Resonance (NMR) by using deuterated water as a deuterated solvent. In result, 1H-NMR spectrum (based on 3-(trimethyl silyl)-1-propane sodium sulfonate) was detected in 4.66 ppm to 4.76 ppm (m, 2H) and 5.38 ppm to 5.41 ppm (m, 1H). In addition, the obtained compound was analyzed by Time of Flight Secondary Ion Mass Spectrometry (TOF-SIMS). In result, the peak of molecular weight corresponding to $C_3H_3SO_6Li_2^+$ as a positive secondary ion was detected, and the peak of molecular weight corresponding to $C_3H_3SO_6^-$ as a negative secondary ion was detected. Accordingly, it was confirmed that the obtained compound was the sulfone compound having a carbonate group and a sulfonyl group shown in Chemical formula 9(1), and the sulfone compound was able to be easily synthesized by an existing synthesizing method.

Example 1-1

The laminated film secondary battery shown in FIG. 7 to FIG. 9 was fabricated by the following procedure. The secondary battery was fabricated as a lithium ion secondary battery in which the capacity of the anode 34 was expressed based on insertion and extraction of lithium.

First, the cathode 33 was formed. First, lithium carbonate ($Li_2CO_3$) and cobalt carbonate ($CoCO_3$) were mixed at a molar ratio of 0.5:1. After that, the mixture was fired in the air at 900 deg C. for 5 hours. Thereby, lithium cobalt complex oxide ($LiCoO_2$) was obtained. Subsequently, 91 parts by mass of the lithium cobalt complex oxide as a cathode active material, 6 parts by mass of graphite as an electrical conductor, and 3 parts by mass of polyvinylidene fluoride as a binder were mixed to obtain a cathode mixture. After that, the cathode mixture was dispersed in N-methyl-2-pyrrolidone to obtain paste cathode mixture slurry. Subsequently, the both faces of the cathode current collector 33A made of a strip-shaped aluminum foil (thickness: 12 µm thick) were uniformly coated with the cathode mixture slurry by a bar coater, which was dried. After that, the resultant was compression-molded by a roll pressing machine to form the cathode active material layer 33B.

Next, the anode 34 was formed. First, the anode current collector 34A made of an electrolytic copper foil (thickness: 10 µm) was prepared. After that, silicon as an anode active material was deposited on the both faces of the anode current collector 34A by electron beam evaporation method to form a plurality of anode active material particles, and thereby the anode active material layer 34B was formed. In the anode active material layer 34B, the anode active material particles were formed by one deposition step so that the anode active material particles had a single layer structure. The thickness of the anode active material layer 34B formed on a single face of the anode current collector 34A was 5 µm. Subsequently, as the sulfone compounds having a carbonate group and a sulfonyl group of the invention, the sulfone compound shown in Chemical formula 9-1 was dissolved in pure water to prepare 3% aqueous solution. Finally, the anode current collector 34A on which the anode active material layer 34B was formed was dipped in the aqueous solution for several seconds, and then taken out, which was dried in the reduced pressure environment at 60 deg C. to form the coat 34C on the anode active material layer 34B.

Next, after ethylene carbonate (EC) and diethyl carbonate (DEC) were mixed as a solvent, lithium hexafluorophosphate (LiPF$_6$) as an electrolyte salt was dissolved therein to prepare an electrolytic solution. The composition of the solvent (EC:DEC) was 30:70 at a weight ratio. The concentration of lithium hexafluorophosphate in the electrolytic solution was 1 mol/kg.

Finally, the secondary battery was assembled by using the cathode 33, the anode 34, and the electrolytic solution. First, the cathode lead 31 made of aluminum was welded to one end of the cathode current collector 33A, and the anode lead 32 made of nickel was welded to one end of the anode current collector 34A. Subsequently, the cathode 33, the separator 35 (thickness: 25 µm) made of a microporous polyethylene film, and the anode 34 were layered in this order. After the resultant laminated body was spirally wound in the longitudinal direction, the end portion of the spirally wound body was fixed by the protective tape 37 made of an adhesive tape, and thereby a spirally wound body as a precursor of the spirally wound electrode body 30 was formed. Subsequently, the spirally wound body was sandwiched between the package members 40 made of a 3-layer laminated film (total thickness: 100 µm) in which a nylon film (thickness: 30 µm), an aluminum foil (thickness: 40 µm), and a non-stretch polypropylene film (thickness 30 µm) were layered from the outside. After that, outer edges other than an edge of one side of the package members were thermally fusion-bonded to each other. Thereby, the spirally wound body was contained in the package members 40 in a pouched state. Subsequently, an electrolytic solution was injected through the opening of the package member 40, the electrolytic solution was impregnated in the separator 35, and thereby the spirally wound electrode body 30 was formed. Finally, the opening of the package member 40 was sealed by thermal fusion bonding in the vacuum atmosphere, and thereby the laminated film secondary battery was completed. For the secondary battery, lithium metal was not precipitated on the anode 34 in a state of full charge by adjusting the thickness of the cathode active material layer 33B so that the charge and discharge capacity of the anode 34 was larger than the charge and discharge capacity of the cathode 33.

Example 1-2

A procedure was performed in the same manner as that of Example 1-1, except that propylene carbonate (PC) was added as a solvent, the composition of the solvent (EC:PC:DEC) was changed to 10:20:70 at a weight ratio.

Example 1-3

A procedure was performed in the same manner as that of Example 1-1, except that 4-fluoro-1,3-dioxolane-2-one (FEC) as a cyclic ester carbonate having halogen shown in Chemical formula 15 was used as a solvent instead of EC, and the composition of the solvent (DEC:FEC) was changed to 70:30 at a weight ratio.

Example 1-4

A procedure was performed in the same manner as that of Example 1-1, except that PC and FEC were added as a solvent, and the composition of the solvent (EC:PC:DEC:FEC) was changed to 10:10:70:10 at a weight ratio.

Example 1-5

A procedure was performed in the same manner as that of Example 1-1, except that 4,5-difluoro-1,3-dioxolane-2-one (DFEC) as a cyclic ester carbonate having halogen shown in Chemical formula 15 was added as a solvent, and the composition of the solvent (EC:DEC:DFEC) was changed to 10:70:20 at a weight ratio.

Example 1-6

A procedure was performed in the same manner as that of Example 1-1, except that PC and DFEC were added as a solvent, and the composition of the solvent (EC:PC:DEC:FEC) was changed to 10:10:70:10 at a weight ratio.

Example 1-7

A procedure was performed in the same manner as that of Example 1-1, except that FEC and bis(fluoromethyl) carbonate (DFDMC) as a chain ester carbonate having halogen shown in Chemical formula 14 were added as a solvent instead of EC, and the composition of the solvent (DEC:FEC:DFDMC) was changed to 65:30:5 at a weight ratio.

Examples 1-8 and 1-9

A procedure was performed in the same manner as that of Example 1-1, except that PC and vinylene carbonate (VC) as a cyclic ester carbonate having an unsaturated bond shown in Chemical formula 11 were added as a solvent, and the composition of the solvent (EC:PC:DEC:VC) was changed to 10:19:70:1 at a weight ratio (Example 1-8) or 10:10:70:10 at a weight ratio (Example 1-9).

Comparative Examples 1-1 to 1-3

A procedure was performed in the same manner as that of Examples 1-1, 1-3, and 1-5, except that the coat 34C was not formed.

The cycle characteristics of the secondary batteries of Examples 1-1 to 1-9 and Comparative examples 1-1 to 1-3 were examined. The results shown in Table 1 were obtained.

In examining the cycle characteristics, charge and discharge were performed two cycles in the atmosphere of 23 deg C., and thereby the discharge capacity was measured. Subsequently, the secondary battery was charged and discharged in the same atmosphere until the total of the number of cycles became 100 cycles to measure the discharge capacity. After that, the discharge capacity retention ratio (%)= (discharge capacity at the 100th cycle/discharge capacity at the second cycle)×100 was calculated. The charge and discharge condition of 1 cycle was as follows. That is, charge was performed at the constant current density of 1 mA/cm$^2$ until the battery voltage reached 4.2 V, charge was performed at the constant voltage of 4.2 V until the current density reached 0.02 mA/cm², and then discharge was performed at the constant current density of 1 mA/cm² until the battery voltage reached 2.5 V.

shown in Chemical formula 11 to Chemical formula 13 was used, or the chain ester carbonate having halogen shown in Chemical formula 14 or the cyclic ester carbonate having halogen shown in Chemical formula 15 was used, the cycle

TABLE 1

Anode active material: silicon (electron beam evaporation method)

| | Anode Coat | Electrolytic solution | | | | | | | Electrolyte salt (mol/kg) | Discharge capacity retention ratio (%) |
| --- | --- | --- | --- | --- | --- | --- | --- | --- | --- | --- |
| | | Solvent (wt %) | | | | | | | | |
| | | EC | PC | DEC | FEC | DFEC | DFDMC | VC | | |
| Example 1-1 | Chemical formula 9(1) | 30 | — | 70 | — | — | — | — | LiPF$_6$: 1 | 42 |
| Example 1-2 | | 10 | 20 | 70 | — | — | — | — | | 37 |
| Example 1-3 | | — | — | 70 | 30 | — | — | — | | 76 |
| Example 1-4 | | 10 | 10 | 70 | 10 | — | — | — | | 68 |
| Example 1-5 | | 10 | — | 70 | — | 20 | — | — | | 78 |
| Example 1-6 | | 10 | 10 | 70 | — | 10 | — | — | | 76 |
| Example 1-7 | | — | — | 65 | 30 | — | 5 | — | | 78 |
| Example 1-8 | | 10 | 19 | 70 | — | — | — | 1 | | 58 |
| Example 1-9 | | 10 | 10 | 70 | — | — | — | 10 | | 61 |
| Comparative example 1-1 | — | 30 | — | 70 | — | — | — | — | LiPF$_6$: 1 | 33 |
| Comparative example 1-2 | | — | — | 70 | 30 | — | — | — | | 72 |
| Comparative example 1-3 | | 10 | — | 70 | — | 20 | — | — | | 75 |

As shown in Table 1, in Examples 1-1 to 1-9 in which the coat 34C was formed, the discharge capacity retention ratio was higher compared to that of Comparative examples 1-1 to 1-3 in which the coat 34C was not formed irrespective of the composition of solvent. The result showed that in the case where the coat 34C was formed, lithium ions were easily inserted in the anode 34 and easily extracted from the anode 34, and the electrolytic solution was difficult to be decomposed even if charge and discharge were repeated.

In this case, focusing attention on the composition of the solvent, in Examples 1-3 to 1-7 containing FEC, DFEC, and DFDMC, the discharge capacity retention ratio was higher than that of Examples 1-1 and 1-2 not containing FEC, DFEC, and DFDMC. In Examples 1-8 and 1-9 containing VC, the discharge capacity retention ratio was higher than that of Examples 1-1 and 1-2 not containing VC. In particular, in Examples 1-3 to 1-7, in the case containing DFEC and DFDMC, the discharge capacity retention ratio was higher than that in the case containing FEC.

Only the result in the case using the cyclic ester carbonate having an unsaturated bond shown in Chemical formula 11 has been herein shown, but results in the case using the cyclic ester carbonate having an unsaturated bond shown in Chemical formula 12 or Chemical formula 13 has not been herein shown. However, the cyclic ester carbonate having an unsaturated bond shown in Chemical formula 12 and the like fulfill a function to suppress decomposition of the electrolytic solution in the same manner as the cyclic ester carbonate having an unsaturated bond shown in Chemical formula 11. Thus, it is evident that in the case using the former, a result similar to that of the case using the latter is obtained.

Accordingly, in the secondary battery of the invention, it was confirmed that in the case where the coat 34C containing the sulfone compound having a carbonate group and a sulfonyl group was provided on the anode active material layer 34B, the cycle characteristics were improved irrespective of the composition of solvent.

Further, it was also confirmed that in the case where as a solvent, the cyclic ester carbonate having an unsaturated bond characteristics were further improved. In particular, in the case where the chain ester carbonate having halogen shown in Chemical formula 14 or the cyclic ester carbonate having halogen shown in Chemical formula 15 was used, the larger the number of halogen was, the higher the effect was.

Examples 2-1 to 2-4

A procedure was performed in the same manner as that of Examples 1-1 and 1-3, except that lithium tetrafluoroborate (LiBF$_4$: Example 2-1), the compound shown in Chemical formula 21(1) as the compound shown in Chemical formula 18 (Example 2-2), the compound shown in Chemical formula 21(6) as the compound shown in Chemical formula 18 (Example 2-3), or the compound shown in Chemical formula 27(2) as the compound shown in Chemical formula 25 (Example 2-4) was added as an electrolyte salt, and the concentration of LiPF$_6$ in the electrolytic solution was 0.9 mol/kg, and the concentration of LiBF$_4$ or the like in the electrolytic solution was 0.1 mol/kg.

Examples 2-5 to 2-7

A procedure was performed in the same manner as that of Example 1-3, except that propene sultone as sultone (PRS: Example 2-5), succinic anhydride as an acid anhydride (SCAH: Example 2-6), or sulfobenzoic anhydride (SBAH: Example 2-7) was added as an additive to the electrolytic solution. The content of PRS or the like in the electrolytic solution was 1 wt %. "1 wt %" means that where the entire solvent was 100 wt %, PRS or the like was added by the amount corresponding to 1 wt %.

For the secondary batteries of Examples 2-1 to 2-7, the cycle characteristics were examined. The results shown in Table 2 were obtained.

TABLE 2

Anode active material: silicon (electron beam evaporation method)

| | Anode Coat | Solvent (wt %) | | | Electrolyte salt (mol/kg) | Others (wt %) | Discharge capacity retention ratio (%) |
|---|---|---|---|---|---|---|---|
| | | EC | DEC | FEC | | | |
| Example 1-1 | Chemical formula 9(1) | 30 | 70 | — | LiPF$_6$: 1 | — | 42 |
| Example 1-3 | | — | 70 | 30 | LiPF$_6$: 1 | — | 76 |
| Example 2-1 | | — | 70 | 30 | LiPF$_6$: 0.9 LiBF$_4$: 0.1 | — | 77 |
| Example 2-2 | | 30 | 70 | — | LiPF$_6$: 0.9 Chemical formula 21(1): 0.1 | — | 44 |
| Example 2-3 | | 30 | 70 | — | LiPF$_6$: 0.9 Chemical formula 21(6): 0.1 | — | 43 |
| Example 2-4 | | — | 70 | 30 | LiPF$_6$: 0.9 Chemical formula 27(2): 0.1 | — | 78 |
| Example 2-5 | | — | 70 | 30 | LiPF$_6$: 1 | PRS: 1 | 77 |
| Example 2-6 | | — | 70 | 30 | | SCAH: 1 | 77 |
| Example 2-7 | | — | 70 | 30 | | SBAH: 1 | 77 |
| Comparative example 1-1 | — | 30 | 70 | — | LiPF$_6$: 1 | — | 33 |
| Comparative example 1-2 | | — | 70 | 30 | | — | 72 |

As shown in Table 2, in the case where LiBF$_4$ or the like was added as an electrolyte salt into the electrolytic solution, or PRS or the like was added as an additive into the electrolytic solution, results similar to the results of Table 1 were obtained. That is, in Examples 2-1 to 2-7 in which the coat 34C was formed, the discharge capacity retention ratio was higher compared to that of Comparative examples 1-1 and 1-2 in which the coat 34C was not formed.

In this case, focusing attention on the type of electrolyte salt, in Examples 2-1 to 2-47 in which LiBF$_4$ or the like was added, the discharge capacity retention ratio was higher than that of Examples 1-1 and 1-3 in which LiBF$_4$ or the like was not added. Further, focusing attention on presence of additive, in Examples 2-5 to 2-7 in which PRS or the like was added, the discharge capacity retention ratio was higher than that of Example 1-3 in which PRS or the like was not added.

Only the results in the case using lithium tetrafluoroborate, the compound shown in Chemical formula 18, or the compound shown in Chemical formula 25 have been herein shown. Results in the case using lithium perchlorate, lithium hexafluoroarsenate, or the compounds shown in Chemical formulas 19, 20, 24, or 26 have not been herein shown. However, lithium perchlorate and the like have a function to increase the discharge capacity retention ratio in the same manner as the lithium tetrafluoroborate and the like. Thus, it is evident that in the case using the former, a result similar to that of the case using the latter is obtained.

Accordingly, in the secondary battery of the invention, it was confirmed that in the case where the coat 34C that contained the sulfone compound having a carbonate group and a sulfonyl group was provided on the anode active material layer 34B, the cycle characteristics were improved even if the type of electrolyte salt was changed or the additive was added into the electrolytic solution.

Further, it was also confirmed that in the case where as an electrolyte salt, lithium phosphate hexafluoride, lithium tetrafluoroborate, lithium perchlorate, or lithium hexafluoroarsenate was used or the compound shown in Chemical formula 18 to chemical formula 20 or Chemical formula 24 to Chemical formula 26 was used, or in the case where sultone or an acid anhydride as an additive of the electrolytic solution was used, the cycle characteristics were further improved.

Examples 3-1 and 3-2

A procedure was performed in the same manner as that of Example 1-3, except that dilithium sulfopropionate as an alkali metal salt (Example 3-1) or magnesium sulfopropionate as an alkali earth metal salt (Example 3-2) was contained in the coat 34C. In forming the coat 34C, a solution obtained by adding 3% of dilithium sulfopropionate or the like to 3% aqueous solution in which the sulfone compound shown in Chemical formula 9(1) was dissolved was used.

Example 3-3

A procedure was performed in the same manner as that of Example 1-3, except that in forming the anode active material layer 34B, after a plurality of anode active material particles were formed, an oxide of silicon (SiO$_2$) as an oxide-containing film was precipitated on the surface of the anode active material particles by liquid-phase precipitation method. In forming the oxide-containing film, the anode current collector 34A on which the anode active material particles were formed was dipped in a solution obtained by dissolving boron as an anion capture agent in hydrofluosilic acid for three hours, the oxide of silicon was precipitated on the surface of the anode active material particles, and then the resultant was washed and dried under reduced pressure.

Example 3-4

A procedure was performed in the same manner as that of Example 1-3, except that in forming the anode active material layer 34B, after a plurality of anode active material particles were formed, a plating film of cobalt (Co) as a metal material was grown by electrolytic plating method. In forming the metal material, a current was applied while air was supplied to a plating bath to deposit cobalt on the both faces of the anode current collector 34A. As a plating solution, a cobalt plating solution (manufactured by Japan Pure Chemical Co., Ltd.) was used. The current density was in the range from 2 A/dm$^2$ to 5 A/dm$^2$, and the plating rate was 10 nm/sec.

Example 3-5

A procedure was performed in the same manner as that of Example 1-3, except that in forming the anode active material layer 34B, after a plurality of anode active material particles were formed, the oxide-containing film and the metal material were formed in this order by the procedure of Examples 3-3 and 3-4.

Comparative Examples 2-1 to 2-3

A procedure was performed in the same manner as that of Examples 3-3 to 3-5, except that the coat 34C was not formed.

For the secondary batteries of Examples 3-1 to 3-3 and Comparative examples 2-1 to 2-3, the cycle characteristics were examined. The results shown in Table 3 were obtained.

sulfonyl group was provided on the anode active material layer 34B, the cycle characteristics were improved even if the alkali metal salt or the alkali earth metal salt was contained in the coat 34C, or even if the oxide-containing film or the metal material was formed before the coat 34C was formed.

Further, it was also confirmed that in the case where the alkali metal salt or the alkali earth metal salt was contained in

TABLE 3

| | Anode active material: silicon (electron beam evaporation method) | | | | | | |
|---|---|---|---|---|---|---|---|
| | Anode | | | Electrolytic solution | | | Discharge |
| | Oxide-containing film | Metal material | Coat | Solvent (wt %) | | Electrolyte salt | capacity retention |
| | | | | DEC | FEC | (mol/kg) | ratio (%) |
| Example 1-3 | — | — | Chemical formula 9(1) | 70 | 30 | LiPF$_6$: 1 | 76 |
| Example 3-1 | | | Chemical formula 9(1) + dilithium sulfopropionate | | | | 82 |
| Example 3-2 | | | Chemical formula 9(1) + magnesium sulfopropionate | | | | 85 |
| Example 3-3 | SiO$_2$ | — | Chemical formula 9(1) | | | | 92 |
| Example 3-4 | — | Co | | | | | 90 |
| Example 3-5 | SiO$_2$ | Co | | | | | 93 |
| Comparative example 2-1 | SiO$_2$ | — | — | 70 | 30 | LiPF$_6$: 1 | 90 |
| Comparative example 2-2 | — | Co | | | | | 88 |
| Comparative example 2-3 | SiO$_2$ | Co | | | | | 91 |

As shown in Table 3, even if the alkali metal salt or the like was contained in the coat 34 or even if the oxide-containing film or the metal material was formed before the coat 34C was formed, results similar to those of Table 1 were obtained. That is, in Examples 3-1 to 3-5 in which the coat 34C was formed, the discharge capacity retention ratio was higher compared to that of Comparative examples 2-1 to 2-3 in which the coat 34C was not formed.

In this case, focusing attention on presence of the alkali metal salt or the like in the coat 34, in Examples 3-1 and 3-2 containing the alkali metal salt or the like, the discharge capacity retention ratio was higher than that of Example 1-3 in which the alkali metal salt or the like was not contained. Further, focusing attention on presence of the oxide-containing film or the metal material, in Examples 3-3 to 3-5 in which the oxide-containing film or the metal material was formed, the discharge capacity retention ratio was higher than that of Example 1-3 in which the oxide-containing film or the metal material was not formed. In particular, in Examples 3-3 to 3-5, in the case forming both the oxide-containing film and the metal material, the discharge capacity retention ratio was higher than that of the case forming one thereof. In the case forming one thereof, the discharge capacity retention ratio in the case forming the oxide-containing film was higher than that of the case forming the metal material. Further, in Examples 3-3 to 3-5, in the case where the oxide-containing film and the metal material were formed, the discharge capacity retention ratio was higher than that of the case where the alkali metal salt or the like was contained in the coat 34C.

Accordingly, in the secondary battery of the invention, it was confirmed that in the case where the coat 34C that contained the sulfone compound having a carbonate group and a the coat 34, or the oxide-containing film or the metal material was formed before the coat 34C was formed, the cycle characteristics were further improved. In particular, in the case where the oxide-containing film or the metal material was formed, the discharge capacity retention ratio was higher than that of the case where the alkali metal salt or the alkali earth metal salt was contained in the coat 34C. In the case where the oxide-containing film or the metal material was formed, the discharge capacity retention ratio in the case forming only the oxide-containing film was higher than that of the case forming only the metal material. In the case forming both the oxide-containing film and the metal material, the discharge capacity retention ratio was higher than that of the case forming one thereof.

Example 4-1

A procedure was performed in the same manner as that of Example 1-3, except that the sulfone compound was contained in the cathode 33 instead of the anode 34. In making the cathode 33 contain the sulfone compound, a coat containing the sulfone compound was formed on the cathode active material layer 33B by a formation procedure similar to that of the coat 34C.

Example 4-2

A procedure was performed in the same manner as that of Example 1-3, except that the sulfone compound was contained in the separator 35 instead of the anode 34. In making the separator 35 contain the sulfone compound, a coat containing the sulfone compound was formed on the both faces of the separator 35 by a formation procedure similar to that of the coat 34C.

Example 4-3

A procedure was performed in the same manner as that of Example 1-3, except that the sulfone compound was contained in the electrolytic solution instead of the anode 34. In making the electrolytic solution contain the sulfone compound, the sulfone compound was dispersed in the electrolytic solution while the dispersion amount was adjusted so that the dispersion amount became similar to the content in the foregoing coat.

For the secondary batteries of Examples 4-1 to 4-3, the cycle characteristics were examined. The results shown in Table 4 were obtained.

TABLE 4

| | Ester compound | | Discharge capacity retention ratio (%) |
|---|---|---|---|
| | Type | Containing location (containing form) | |
| Example 1-3 | Chemical formula 9(1) | Anode (coat) | 76 |
| Example 4-1 | | Cathode (coat) | 74 |
| Example 4-2 | | Separator (coat) | 74 |
| Example 4-3 | | Electrolytic solution (dispersion) | 73 |
| Comparative example 1-2 | — | — | 72 |

As shown in Table 4, in Examples 4-1 to 4-3 in which the sulfone compound was contained in the cathode 33, the separator 35, or the electrolytic solution, the discharge capacity retention ratio was higher than that of Comparative example 1-2 in the same manner as in Example 1-3 in which the sulfone compound was contained in the anode 34. In this case, in the case where comparison was made among Examples 1-3 and 4-1 to 4-3 in which the containing location of the sulfone compound was different from each other, the discharge capacity retention ratio in the case where the sulfone compound was contained in the cathode 33 or the separator 35 was higher than that in the case where the sulfone compound was contained in the electrolytic solution. The discharge capacity retention ratio was higher in the case where the sulfone compound was contained in the anode 34.

Only the results in the case where the sulfone compound was contained in only one of the cathode 33, the anode 34, the separator 35, and the electrolytic solution have been herein shown, but results in the case where the sulfone compound was contained in two or more components thereof have not been herein shown. However, it is evident that the discharge capacity retention ratio is improved in the case where any one component thereof contains the sulfone compound. Further, there is no particular reason that the discharge capacity retention ratio is lowered in the case where the sulfone compound is contained in two or more components. Therefore, it is evident that in the case where the sulfone compound is contained in two or more components, a result similar to that in the case where the sulfone compound is contained in any one of the components is obtained as well.

Accordingly, in the secondary battery of the invention, it was confirmed that in the case where the sulfone compound having a carbonate group and a sulfonyl group was contained in at least one of the cathode 33, the anode 34, the separator 35, and the electrolytic solution, the cycle characteristics were improved.

As evidenced by the results of Table 1 to Table 4, in the secondary battery of the invention, it was confirmed that in the case where the sulfone compound having a carbonate group and a sulfonyl group was contained in at least one of the cathode, the anode, the separator, and the electrolytic solution, the cycle characteristics were improved irrespective of the composition of solvent, the type of electrolyte salt, presence of an additive in the electrolytic solution or the like. Specially, it was confirmed that in the case where the foregoing sulfone compound was contained in the anode, the cycle characteristics were further improved.

The invention has been described with reference to the embodiment and the examples. However, the invention is not limited to the aspects described in the foregoing embodiment and the foregoing examples, and various modifications may be made. For example, usage applications of the sulfone compound or the anode of the invention are not limited to the battery, but may include electrochemical devices other than the battery. As other usage application, for example, a capacitor and the like are cited.

In the foregoing embodiment and the foregoing examples, the description has been given of the lithium ion secondary battery in which the anode capacity is expressed based on inserting and extracting lithium as a battery type. However, the battery of the invention is not limited thereto. The invention is similarly applicable to a lithium metal secondary battery in which lithium metal is used as an anode active material and the anode capacity is expressed based on precipitation and dissolution of lithium, or a secondary battery in which the anode capacity includes the capacity associated with insertion and extraction of lithium and the capacity associated with precipitation and dissolution of lithium, and the anode capacity is expressed by the sum of these capacities, by setting the charge capacity of the anode material capable of inserting and extracting lithium to a smaller value than that of the charge capacity of the cathode. In the case where the battery of the invention is applied to the lithium metal secondary battery, for example, as a solvent used for preparing the solution containing the sulfone compound, a nonaqueous solvent or the like having high polarity or the like is able to be used.

Further, in the foregoing embodiment and the foregoing examples, the description has been given of the case using the electrolytic solution or the gelatinous electrolyte in which an electrolytic solution is held by a polymer compound as an electrolyte of the battery of the invention. However, other type of electrolyte may be used. As other electrolyte, for example, a mixture obtained by mixing an ion conductive inorganic compound such as ion conductive ceramics, ion conductive glass, and ionic crystal and an electrolytic solution; a mixture obtained by mixing other inorganic compound and an electrolytic solution; a mixture of the foregoing inorganic compound and a gelatinous electrolyte and the like are cited.

Further, in the foregoing embodiment and the foregoing examples, the description has been given with the specific examples of the cylindrical or laminated film secondary battery as a battery structure, and with the specific example in which the battery element has the spirally wound structure as a battery structure. However, the battery of the invention is e similarly applicable to a battery having other structure such as a square battery, a coin type battery, and a button type battery or a battery in which the battery element has other structure such as a lamination structure.

Further, in the foregoing embodiment and the foregoing examples, the description has been given of the case using lithium as an electrode reactant. However, as an electrode reactant, other Group 1 element such as sodium (Na) and potassium (K), a Group 2 element such as magnesium (Mg) and calcium (Ca), or other light metal such as aluminum may be used. In this case, the anode material described in the foregoing embodiment is able to be used as an anode active material as well.

It should be understood by those skilled in the art that various modifications, combinations, sub-combinations and alternations may occur depending on design requirements and other factors insofar as they are within the scope of the appended claims or the equivalents thereof.

What is claimed is:

1. A secondary battery comprising:
a cathode and an anode oppositely arranged with a separator in between; and
an electrolytic solution,
wherein,
the cathode comprises a coating layer on an cathode active material layer on a cathode current collector,
the anode comprises a coating layer on an anode active material layer on an anode current collector, and
at least one of the coating layer of the cathode and coating layer of the anode is made from a material including a sulfone compound having a carbonate group and a sulfonyl group.

2. The secondary battery according to claim 1, wherein the coating layer of the anode contains at least one of an alkali metal salt and an alkali earth metal salt except for a compound corresponding to the sulfone compound.

3. The secondary battery according to claim 1, wherein the anode active material layer contains an anode active material containing at least one of a simple substance of silicon, an alloy of silicon, a compound of silicon, a simple substance of tin, an alloy of tin, and a compound of tin.

4. The secondary battery according to claim 1, wherein the anode active material layer has a plurality of anode active material particles, and has an oxide-containing film covering a surface of the anode active material particles.

5. The secondary battery according to claim 4, wherein the oxide-containing film contains an oxide of at least one of silicon, germanium, and tin.

6. The secondary battery according to claim 1, wherein:
the anode active material layer has a plurality of anode active material particles, and
a metal material not being alloyed with an electrode reactant in a gap between the anode active material particles.

7. The secondary battery according to claim 6, wherein:
the anode active material particles have a multilayer structure in the particles, and
the anode active material layer has the metal material in a gap in the anode active material particles.

8. The secondary battery according to claim 6, wherein the metal material is at least one of iron, cobalt, nickel, zinc, and copper.

* * * * *